(12) United States Patent
Nobles

(10) Patent No.: US 11,779,324 B2
(45) Date of Patent: Oct. 10, 2023

(54) SUTURING METHODS AND APPARATUSES

(71) Applicant: Med-Venture Investments, LLC, Fountain Valley, CA (US)

(72) Inventor: Anthony A. Nobles, St. Thomas, VI (US)

(73) Assignee: Med-Venture Investments, LLC, Fountain Valley, CA (US)

( * ) Notice: Subject to any disclaimer, the term of this patent is extended or adjusted under 35 U.S.C. 154(b) by 571 days.

(21) Appl. No.: 16/688,671

(22) Filed: Nov. 19, 2019

(65) Prior Publication Data

US 2020/0253602 A1 Aug. 13, 2020

Related U.S. Application Data

(62) Division of application No. 15/101,607, filed as application No. PCT/US2014/068742 on Dec. 5, 2014, now Pat. No. 10,512,458.

(60) Provisional application No. 61/912,705, filed on Dec. 6, 2013.

(51) Int. Cl.
*A61B 17/04* (2006.01)
*A61B 17/062* (2006.01)
*A61B 17/00* (2006.01)
*A61B 17/06* (2006.01)

(52) U.S. Cl.
CPC ........ *A61B 17/0469* (2013.01); *A61B 17/062* (2013.01); *A61B 2017/00314* (2013.01); *A61B 2017/06042* (2013.01)

(58) Field of Classification Search
CPC ............ A61B 17/0469; A61B 17/0491; A61B 17/062; A61B 2017/0472; A61B 2017/0477; A61B 2017/0498; A61B 2017/06042

See application file for complete search history.

(56) References Cited

U.S. PATENT DOCUMENTS

| | | |
|---|---|---|
| 118,683 A | 9/1871 | Bruce |
| 1,064,307 A | 6/1913 | Fleming |
| 1,593,347 A | 7/1926 | Nardi |
| 1,822,330 A | 9/1931 | Ainslie |
| 1,989,919 A | 2/1935 | Everitt |
| 2,348,218 A | 5/1944 | Karle |

(Continued)

FOREIGN PATENT DOCUMENTS

| | | |
|---|---|---|
| AU | 2006251579 | 11/2006 |
| CN | 101495049 | 12/2010 |

(Continued)

OTHER PUBLICATIONS

Advances in Vascular Surgery, by John S. Najarian, M.D. and John P. Delaney, M.D., copyright 1983 by Year Book Publishers, Inc. at pp. 94,95,96, and 224.

(Continued)

*Primary Examiner* — Sarah A Long
(74) *Attorney, Agent, or Firm* — Knobbe, Martens, Olson & Bear LLP

(57) ABSTRACT

Suturing devices, systems, and methods used to suture biological structures. The suturing devices can be configured to place sutures into body tissue from one side of the tissue without requiring a component on an opposite side of the tissue and without requiring insertion of components into the body tissue beyond the needles and the suture.

11 Claims, 16 Drawing Sheets

(56) References Cited

U.S. PATENT DOCUMENTS

| | | | |
|---|---|---|---|
| 2,473,742 | A | 6/1949 | Auzin |
| 2,548,602 | A | 4/1951 | Greenburg |
| 2,601,564 | A | 6/1952 | Smith |
| 2,637,290 | A | 5/1953 | Sigoda |
| 2,738,790 | A | 3/1956 | Todt, Sr. et al. |
| 2,741,225 | A | 4/1956 | Fink |
| 2,741,226 | A | 4/1956 | Dietrich et al. |
| 2,748,748 | A | 6/1956 | Lovejoy |
| 2,790,422 | A | 4/1957 | Grumbach |
| 2,849,002 | A | 8/1958 | Oddo |
| 2,945,460 | A | 7/1960 | Kagiyama |
| 2,959,172 | A | 11/1960 | Held |
| 2,988,055 | A | 6/1961 | Platt |
| 3,098,467 | A | 7/1963 | Nagele, Jr. |
| 3,107,654 | A | 10/1963 | Fehrenback |
| 3,241,554 | A | 3/1966 | Coanda |
| 3,260,242 | A | 7/1966 | Liguori |
| 3,262,427 | A | 7/1966 | Von Arx |
| 3,292,627 | A | 12/1966 | Harautuneian |
| 3,294,068 | A | 12/1966 | Hechtle |
| 3,301,221 | A | 1/1967 | Von Arx |
| 3,394,705 | A | 7/1968 | Abramson |
| 3,664,345 | A | 5/1972 | Dabbs et al. |
| 3,665,926 | A | 5/1972 | Flores |
| 3,774,596 | A | 11/1973 | Cook |
| 3,828,790 | A | 8/1974 | Curtiss et al. |
| 3,831,587 | A | 8/1974 | Boyd |
| 3,842,840 | A | 10/1974 | Schweizer |
| 3,877,434 | A | 4/1975 | Ferguson et al. |
| 3,882,852 | A | 5/1975 | Sinnreich |
| 3,882,855 | A | 5/1975 | Schulte et al. |
| 3,888,117 | A | 6/1975 | Lewis |
| 3,903,893 | A | 9/1975 | Scheer |
| 3,946,740 | A | 3/1976 | Bassett |
| 3,946,741 | A | 3/1976 | Adair |
| 3,952,742 | A | 4/1976 | Taylor |
| 3,976,079 | A | 8/1976 | Samuels |
| 3,989,389 | A | 11/1976 | Hashimoto et al. |
| 4,022,535 | A | 5/1977 | Ritter |
| 4,052,980 | A | 10/1977 | Grams et al. |
| RE29,703 | E | 7/1978 | Fatt |
| 4,107,953 | A | 8/1978 | Casillo |
| 4,119,100 | A | 10/1978 | Rickett |
| 4,164,225 | A | 8/1979 | Johnson et al. |
| 4,168,708 | A | 9/1979 | Lepley et al. |
| 4,204,541 | A | 5/1980 | Kapitanov |
| 4,230,119 | A | 10/1980 | Blum |
| 4,291,698 | A | 9/1981 | Fuchs et al. |
| 4,299,237 | A | 11/1981 | Foti |
| 4,307,722 | A | 12/1981 | Evans |
| 4,345,601 | A | 8/1982 | Fukuda |
| 4,351,342 | A | 9/1982 | Wiita et al. |
| 4,417,532 | A | 11/1983 | Yasukata |
| 4,423,725 | A | 1/1984 | Baran et al. |
| 4,447,227 | A | 5/1984 | Kotsanis |
| 4,457,300 | A | 7/1984 | Budde |
| 4,484,580 | A | 11/1984 | Nomoto et al. |
| 4,512,338 | A | 4/1985 | Balko et al. |
| 4,546,759 | A | 10/1985 | Solar |
| 4,553,543 | A | 11/1985 | Amarasinghe |
| 4,573,966 | A | 3/1986 | Weikl et al. |
| 4,589,868 | A | 5/1986 | Dretler |
| 4,610,662 | A | 9/1986 | Weikl et al. |
| 4,617,738 | A | 10/1986 | Kopacz |
| 4,641,652 | A | 2/1987 | Hutterer et al. |
| 4,662,068 | A | 5/1987 | Polonsky |
| 4,664,114 | A | 5/1987 | Ghodsian |
| 4,734,094 | A | 3/1988 | Jacob et al. |
| 4,744,364 | A | 5/1988 | Kensey |
| 4,750,492 | A | 6/1988 | Jacobs |
| 4,771,776 | A | 9/1988 | Powell et al. |
| 4,774,091 | A | 9/1988 | Yamahira et al. |
| 4,794,928 | A | 1/1989 | Kletschka |
| 4,795,427 | A | 1/1989 | Helzel |
| 4,796,629 | A | 1/1989 | Grayzel |
| 4,824,436 | A | 4/1989 | Wolinsky |
| 4,827,931 | A | 5/1989 | Longmore |
| 4,841,888 | A | 6/1989 | Mills et al. |
| 4,861,330 | A | 8/1989 | Voss |
| 4,898,168 | A | 2/1990 | Yule |
| 4,904,238 | A | 2/1990 | Williams |
| 4,923,461 | A | 5/1990 | Caspari et al. |
| 4,926,860 | A | 5/1990 | Stice et al. |
| 4,932,956 | A | 6/1990 | Reddy et al. |
| 4,935,027 | A | 6/1990 | Yoon |
| 4,946,463 | A | 8/1990 | Wright |
| 4,954,126 | A | 9/1990 | Wallsten |
| 4,957,498 | A | 9/1990 | Caspari et al. |
| 4,972,845 | A | 11/1990 | Iversen et al. |
| 4,981,149 | A | 1/1991 | Yoon et al. |
| 4,983,116 | A | 1/1991 | Koga |
| 4,984,564 | A | 1/1991 | Yuen |
| 4,988,339 | A | 1/1991 | Vadher |
| 4,994,070 | A | 2/1991 | Waters |
| 5,002,531 | A | 3/1991 | Bonzel |
| 5,021,059 | A | 6/1991 | Kensey et al. |
| 5,037,428 | A | 8/1991 | Picha et al. |
| 5,037,433 | A | 8/1991 | Wilk et al. |
| 5,057,114 | A | 10/1991 | Wittich et al. |
| 5,059,201 | A | 10/1991 | Asnis |
| 5,065,772 | A | 11/1991 | Cox, Jr. |
| 5,074,871 | A | 12/1991 | Groshong |
| 5,078,743 | A | 1/1992 | Mikalov et al. |
| 5,090,958 | A | 2/1992 | Sahota |
| 5,100,418 | A | 3/1992 | Yoon et al. |
| 5,104,394 | A | 4/1992 | Knoepfler |
| 5,106,363 | A | 4/1992 | Nobuyoshi |
| 5,108,416 | A | 4/1992 | Ryan et al. |
| 5,108,419 | A | 4/1992 | Reger et al. |
| 5,108,421 | A | 4/1992 | Fowler |
| 5,116,305 | A | 5/1992 | Milder et al. |
| 5,122,122 | A | 6/1992 | Allgood |
| 5,129,883 | A | 7/1992 | Black |
| 5,133,724 | A | 7/1992 | Wilson et al. |
| 5,135,484 | A | 8/1992 | Wright |
| 5,152,769 | A | 10/1992 | Baber |
| 5,160,339 | A | 11/1992 | Chen et al. |
| 5,163,906 | A | 11/1992 | Ahmadi |
| 5,167,223 | A | 12/1992 | Koros et al. |
| 5,171,251 | A | 12/1992 | Bregen et al. |
| 5,171,259 | A | 12/1992 | Inoue |
| 5,174,300 | A | 12/1992 | Bales et al. |
| 5,176,691 | A | 1/1993 | Pierce |
| 5,192,301 | A | 3/1993 | Kamiya et al. |
| 5,196,025 | A | 3/1993 | Ranalletta et al. |
| 5,201,760 | A | 4/1993 | West |
| 5,222,508 | A | 6/1993 | Contarini |
| 5,222,941 | A | 6/1993 | Don Michael |
| 5,222,974 | A | 6/1993 | Kensey et al. |
| 5,224,948 | A | 7/1993 | Abe et al. |
| 5,236,443 | A | 8/1993 | Sontag |
| 5,242,459 | A | 9/1993 | Buelna |
| 5,254,126 | A | 10/1993 | Filipi et al. |
| 5,269,791 | A | 12/1993 | Mayzels et al. |
| 5,281,234 | A | 1/1994 | Wilk et al. |
| 5,281,237 | A | 1/1994 | Gimpelson |
| 5,282,827 | A | 2/1994 | Kensey et al. |
| 5,286,259 | A | 2/1994 | Ganguly et al. |
| 5,290,249 | A | 3/1994 | Foster et al. |
| 5,291,639 | A | 3/1994 | Baum et al. |
| 5,300,106 | A | 4/1994 | Dahl et al. |
| 5,304,184 | A | 4/1994 | Hathaway et al. |
| 5,308,323 | A | 5/1994 | Sogawa et al. |
| 5,312,344 | A | 5/1994 | Grinfeld |
| 5,314,409 | A | 5/1994 | Sarosiek et al. |
| 5,320,604 | A | 6/1994 | Walker et al. |
| 5,320,632 | A | 6/1994 | Heidmueller |
| 5,323,789 | A | 6/1994 | Berggren et al. |
| 5,330,446 | A | 7/1994 | Weldon et al. |
| 5,330,497 | A | 7/1994 | Freitas et al. |
| 5,331,975 | A | 7/1994 | Bonutti |
| 5,336,229 | A | 8/1994 | Noda |
| 5,336,231 | A | 8/1994 | Adair |
| 5,337,736 | A | 8/1994 | Reddy |

(56) References Cited

U.S. PATENT DOCUMENTS

| | | |
|---|---|---|
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,387,221 A | 2/1995 | Bisgaard |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,568 A | 12/1995 | Scott |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,503,634 A | 4/1996 | Christy |
| 5,507,754 A | 4/1996 | Green et al. |
| 5,507,755 A | 4/1996 | Gresl et al. |
| 5,507,757 A | 4/1996 | Sauer et al. |
| 5,514,159 A | 5/1996 | Matula et al. |
| 5,520,609 A | 5/1996 | Moll et al. |
| 5,520,702 A | 5/1996 | Sauer et al. |
| 5,520,703 A | 5/1996 | Essig et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,618 A | 8/1996 | Fleenor et al. |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,685 A | 10/1996 | Mollenauer et al. |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,571,167 A | 11/1996 | Maginot |
| 5,573,540 A | 11/1996 | Yoon |
| 5,578,044 A | 11/1996 | Gordon et al. |
| 5,584,803 A | 12/1996 | Stevens et al. |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,662,664 A | 9/1997 | Gordon et al. |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Amnbrosio |
| 5,700,273 A | 12/1997 | Buelna et al. |
| 5,700,276 A | 12/1997 | Benecke |
| 5,700,277 A | 12/1997 | Nash et al. |
| 5,707,379 A | 1/1998 | Fleenor et al. |
| 5,709,693 A | 1/1998 | Taylor |
| 5,713,910 A | 2/1998 | Gordon et al. |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,728,133 A | 3/1998 | Kontos |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,836,956 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |

(56) References Cited

U.S. PATENT DOCUMENTS

| | | | |
|---|---|---|---|
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,868,764 A | 2/1999 | Rosengart |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,924,424 A | 7/1999 | Stevens et al. |
| 5,925,054 A | 7/1999 | Taylor et al. |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,947,919 A | 9/1999 | Krueger et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,042,601 A | 3/2000 | Smith |
| 6,048,351 A | 4/2000 | Gordon et al. |
| 6,056,760 A | 5/2000 | Koike |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,276 A | 6/2000 | Kontos |
| 6,077,277 A | 6/2000 | Mollenauer et al. |
| 6,077,279 A | 6/2000 | Kontos |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,165,196 A | 12/2000 | Stack et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,254,620 B1 | 7/2001 | Koh et al. |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,443,962 B1* | 9/2002 | Gaber ............... A61B 17/0491 606/139 |
| 6,468,293 B2 | 10/2002 | Bonutti et al. |
| 6,482,171 B1 | 11/2002 | Corvi et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,695,859 B1 | 2/2004 | Golden et al. |
| 6,712,831 B1 | 3/2004 | Kaplan et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,840,246 B2 | 1/2005 | Downing |
| 6,978,176 B2 | 1/2005 | Lattouf |
| 6,855,157 B2 | 2/2005 | Foerster et al. |
| 6,887,249 B1 | 5/2005 | Houser et al. |
| 6,893,448 B2 | 5/2005 | O'Quinn et al. |
| 6,896,686 B2 | 5/2005 | Weber |
| 6,911,034 B2 | 6/2005 | Nobles et al. |
| 6,913,600 B2 | 7/2005 | Valley et al. |
| 6,932,827 B2 | 8/2005 | Cole |
| 6,936,057 B1 | 8/2005 | Nobles |
| 6,964,668 B2 | 11/2005 | Modesitt et al. |
| 6,991,635 B2 | 1/2006 | Takamoto |
| 7,004,952 B2 | 2/2006 | Nobles et al. |
| 7,063,710 B2 | 6/2006 | Takamoto |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,232,448 B2 | 6/2007 | Battles |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,544,199 B2 | 6/2009 | Bain |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,704,261 B2 | 4/2010 | Sakamoto |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |

(56) References Cited

U.S. PATENT DOCUMENTS

| | | | |
|---|---|---|---|
| 7,931,641 B2 | 4/2011 | Chang et al. | |
| 7,935,128 B2 | 5/2011 | Rioux | |
| 7,993,368 B2 | 8/2011 | Gambale et al. | |
| 8,075,573 B2 | 12/2011 | Gambale et al. | |
| 8,083,754 B2 | 12/2011 | Pantages et al. | |
| 8,100,922 B2 * | 1/2012 | Griffith | A61B 17/0469 606/144 |
| 8,105,355 B2 | 1/2012 | Page et al. | |
| 8,152,821 B2 | 4/2012 | Gambale | |
| 8,197,497 B2 | 6/2012 | Nobles et al. | |
| 8,197,510 B2 | 6/2012 | Nobles | |
| 8,202,281 B2 | 6/2012 | Voss | |
| 8,246,636 B2 | 8/2012 | Nobles et al. | |
| 8,252,005 B2 | 8/2012 | Findlay, III et al. | |
| 8,282,659 B2 | 10/2012 | Oren et al. | |
| 8,287,556 B2 | 10/2012 | Gilkey et al. | |
| 8,298,291 B2 | 10/2012 | Ewers et al. | |
| 8,303,622 B2 | 11/2012 | Alkhatib | |
| 8,313,498 B2 | 11/2012 | Pantages | |
| 8,348,962 B2 | 1/2013 | Nobles et al. | |
| 8,372,089 B2 | 2/2013 | Nobles et al. | |
| 8,398,676 B2 | 3/2013 | Roorda et al. | |
| 8,430,893 B2 | 4/2013 | Ma | |
| 8,465,500 B2 | 6/2013 | Speziali | |
| 8,469,975 B2 | 6/2013 | Nobles et al. | |
| 8,496,676 B2 | 7/2013 | Nobles et al. | |
| 8,500,776 B2 | 8/2013 | Ebner | |
| 8,540,736 B2 | 9/2013 | Gaynor et al. | |
| 8,568,427 B2 | 10/2013 | Nobles et al. | |
| 8,623,036 B2 | 1/2014 | Harrison et al. | |
| 8,679,139 B2 | 3/2014 | Aguirre et al. | |
| 8,709,020 B2 | 4/2014 | Nobles | |
| 8,728,105 B2 | 5/2014 | Aguirre | |
| 8,758,370 B2 | 6/2014 | Shikhman et al. | |
| 8,771,296 B2 | 7/2014 | Nobles et al. | |
| 9,078,752 B2 | 7/2015 | Hasenkam | |
| 9,125,632 B2 | 9/2015 | Loulmet | |
| 9,131,938 B2 | 9/2015 | Nobles et al. | |
| 9,326,764 B2 | 5/2016 | Nobles et al. | |
| 9,332,976 B2 | 5/2016 | Yribarren | |
| 9,364,238 B2 | 6/2016 | Bakos et al. | |
| 9,398,907 B2 | 7/2016 | Nobles et al. | |
| 9,402,605 B2 | 8/2016 | Viola | |
| 9,572,667 B2 | 2/2017 | Solem | |
| 9,649,106 B2 | 5/2017 | Nobles et al. | |
| 9,706,988 B2 | 7/2017 | Nobles et al. | |
| 10,178,993 B2 | 1/2019 | Nobles et al. | |
| 10,182,802 B2 | 1/2019 | Nobles et al. | |
| 10,194,902 B2 | 2/2019 | Nobles et al. | |
| 10,285,687 B2 | 5/2019 | Nobles et al. | |
| 10,420,545 B2 | 9/2019 | Nobles et al. | |
| 10,512,458 B2 | 12/2019 | Nobles | |
| 10,610,216 B2 | 4/2020 | Nobles et al. | |
| 10,624,629 B2 | 4/2020 | Nobles et al. | |
| 10,687,801 B2 | 6/2020 | Nobles et al. | |
| 10,758,223 B2 | 9/2020 | Nobles et al. | |
| 10,828,022 B2 | 11/2020 | Nobles et al. | |
| 11,051,802 B2 | 7/2021 | Nobles et al. | |
| 11,197,661 B2 | 12/2021 | Nobles et al. | |
| 11,202,624 B2 | 12/2021 | Nobles | |
| 11,395,658 B2 | 7/2022 | Nobles et al. | |
| 2001/0021854 A1 | 9/2001 | Donnez et al. | |
| 2001/0031973 A1 | 10/2001 | Nobles et al. | |
| 2001/0049492 A1 | 12/2001 | Frazier et al. | |
| 2002/0013601 A1 | 1/2002 | Nobles et al. | |
| 2002/0045908 A1 | 4/2002 | Nobles et al. | |
| 2002/0049453 A1 | 4/2002 | Nobles et al. | |
| 2002/0087178 A1 | 7/2002 | Nobles et al. | |
| 2002/0096183 A1 | 7/2002 | Stevens et al. | |
| 2002/0111653 A1 | 8/2002 | Foerster | |
| 2002/0128598 A1 | 9/2002 | Nobles | |
| 2002/0169475 A1 | 11/2002 | Gainor et al. | |
| 2002/0183787 A1 | 12/2002 | Wahr et al. | |
| 2003/0078601 A1 | 4/2003 | Skikhman et al. | |
| 2003/0114863 A1 | 6/2003 | Field et al. | |
| 2003/0120287 A1 | 6/2003 | Gross et al. | |
| 2003/0144673 A1 | 7/2003 | Onuki et al. | |
| 2003/0195539 A1 | 10/2003 | Attinger et al. | |
| 2003/0204205 A1 | 10/2003 | Sauer et al. | |
| 2003/0208209 A1 | 11/2003 | Gambale et al. | |
| 2003/0220667 A1 | 11/2003 | van der Burg et al. | |
| 2004/0015177 A1 | 1/2004 | Chu | |
| 2004/0044365 A1 | 3/2004 | Bachman | |
| 2004/0059351 A1 | 3/2004 | Eigler et al. | |
| 2004/0068273 A1 | 4/2004 | Fariss et al. | |
| 2004/0102797 A1 | 5/2004 | Golden et al. | |
| 2004/0153116 A1 | 8/2004 | Nobles | |
| 2004/0236356 A1 | 11/2004 | Rioux et al. | |
| 2004/0260298 A1 | 12/2004 | Kaiseer et al. | |
| 2005/0033361 A1 | 2/2005 | Galdonik et al. | |
| 2005/0059984 A1 | 3/2005 | Chanduszko | |
| 2005/0070923 A1 | 3/2005 | McIntosh | |
| 2005/0149066 A1 | 7/2005 | Stafford | |
| 2005/0187575 A1 | 8/2005 | Hallbeck et al. | |
| 2005/0203564 A1 | 9/2005 | Nobles | |
| 2005/0228407 A1 | 10/2005 | Nobles et al. | |
| 2005/0261708 A1 | 11/2005 | Pasricha et al. | |
| 2005/0261710 A1 | 11/2005 | Sakamoto et al. | |
| 2005/0277986 A1 | 12/2005 | Foerster et al. | |
| 2005/0288690 A1 | 12/2005 | Bourque et al. | |
| 2006/0052813 A1 | 3/2006 | Nobles | |
| 2006/0064113 A1 | 3/2006 | Nakao | |
| 2006/0064115 A1 | 3/2006 | Allen et al. | |
| 2006/0069397 A1 | 3/2006 | Nobles et al. | |
| 2006/0074484 A1 | 4/2006 | Huber | |
| 2006/0095052 A1 | 5/2006 | Chambers | |
| 2006/0195120 A1 | 8/2006 | Nobles et al. | |
| 2006/0206146 A1 | 9/2006 | Tenerz | |
| 2006/0248691 A1 | 11/2006 | Rosemann | |
| 2006/0259046 A1 | 11/2006 | de la Torre | |
| 2006/0265010 A1 | 11/2006 | Paraschac et al. | |
| 2006/0282088 A1 | 12/2006 | Ryan | |
| 2006/0282094 A1 | 12/2006 | Stokes et al. | |
| 2006/0282102 A1 | 12/2006 | Nobles et al. | |
| 2006/0287657 A1 | 12/2006 | Bachman | |
| 2007/0005079 A1 | 1/2007 | Zarbatany et al. | |
| 2007/0010829 A1 | 1/2007 | Nobles et al. | |
| 2007/0043385 A1 | 2/2007 | Nobles et al. | |
| 2007/0049952 A1 | 3/2007 | Weiss | |
| 2007/0060930 A1 | 3/2007 | Hamilton et al. | |
| 2007/0106310 A1 | 5/2007 | Goldin et al. | |
| 2007/0118151 A1 | 5/2007 | Davidson | |
| 2007/0142846 A1 | 6/2007 | Catanese, III et al. | |
| 2007/0213757 A1 | 9/2007 | Boraiah | |
| 2007/0219630 A1 | 9/2007 | Chu | |
| 2007/0276413 A1 | 11/2007 | Nobles | |
| 2007/0276414 A1 | 11/2007 | Nobles | |
| 2008/0027468 A1 | 1/2008 | Fenton | |
| 2008/0033459 A1 | 2/2008 | Shafi et al. | |
| 2008/0065145 A1 | 3/2008 | Carpenter | |
| 2008/0077162 A1 | 3/2008 | Domingo | |
| 2008/0091220 A1 | 4/2008 | Chu | |
| 2008/0114384 A1 | 5/2008 | Chang et al. | |
| 2008/0188873 A1 | 8/2008 | Speziali | |
| 2008/0228201 A1 | 9/2008 | Zarbatany | |
| 2008/0269786 A1 | 10/2008 | Nobles et al. | |
| 2008/0269788 A1 | 10/2008 | Phillips | |
| 2009/0036906 A1 | 2/2009 | Stafford | |
| 2009/0048615 A1 | 2/2009 | McIntosh | |
| 2009/0062851 A1 * | 3/2009 | Rosenblatt | A61B 17/0487 606/228 |
| 2009/0099410 A1 | 4/2009 | De Marchena | |
| 2009/0105729 A1 | 4/2009 | Zentgraf | |
| 2009/0105751 A1 | 4/2009 | Zentgraf | |
| 2009/0118726 A1 | 5/2009 | Auth et al. | |
| 2009/0125042 A1 | 5/2009 | Mouw | |
| 2009/0287183 A1 | 11/2009 | Bishop et al. | |
| 2009/0299406 A1 | 12/2009 | Swain et al. | |
| 2009/0299409 A1 | 12/2009 | Coe et al. | |
| 2009/0312772 A1 | 12/2009 | Chu | |
| 2009/0312783 A1 | 12/2009 | Whayne et al. | |
| 2009/0312789 A1 | 12/2009 | Kassab et al. | |
| 2010/0016870 A1 | 1/2010 | Campbell | |
| 2010/0030242 A1 | 2/2010 | Nobles et al. | |

(56) References Cited

U.S. PATENT DOCUMENTS

| | | | |
|---|---|---|---|
| 2010/0042147 A1 | 2/2010 | Janovsky et al. | |
| 2010/0063586 A1 | 3/2010 | Hasenkam et al. | |
| 2010/0087838 A1 | 4/2010 | Nobles et al. | |
| 2010/0094314 A1 | 4/2010 | Hernlund et al. | |
| 2010/0100167 A1 | 4/2010 | Bortlein et al. | |
| 2010/0179585 A1 | 7/2010 | Carpenter et al. | |
| 2010/0185234 A1 | 7/2010 | Fortson et al. | |
| 2010/0210899 A1 | 8/2010 | Schankereli | |
| 2010/0280530 A1* | 11/2010 | Hashiba | A61B 1/0008 606/144 |
| 2011/0011917 A1 | 1/2011 | Loulmet | |
| 2011/0071626 A1 | 3/2011 | Wright | |
| 2011/0190793 A1* | 8/2011 | Nobles | A61B 17/0469 606/144 |
| 2011/0202077 A1 | 8/2011 | Chin et al. | |
| 2011/0208214 A1 | 8/2011 | Poo et al. | |
| 2011/0224720 A1 | 9/2011 | Kassab et al. | |
| 2011/0251627 A1 | 10/2011 | Hamilton et al. | |
| 2011/0288637 A1 | 11/2011 | De Marchena | |
| 2012/0016384 A1 | 1/2012 | Wilke et al. | |
| 2012/0035628 A1 | 2/2012 | Aguirre et al. | |
| 2012/0059398 A1 | 3/2012 | Pate et al. | |
| 2012/0143222 A1 | 6/2012 | Dravis et al. | |
| 2012/0165838 A1 | 6/2012 | Kobylewski et al. | |
| 2012/0296373 A1 | 11/2012 | Roorda et al. | |
| 2012/0303046 A1* | 11/2012 | Stone | A61B 17/0485 606/145 |
| 2013/0103056 A1 | 4/2013 | Chu | |
| 2013/0253542 A1* | 9/2013 | Ostrovsky | A61B 17/062 606/145 |
| 2013/0261645 A1 | 10/2013 | Nobles et al. | |
| 2013/0324800 A1 | 12/2013 | Cahill | |
| 2014/0148825 A1 | 5/2014 | Nobles et al. | |
| 2014/0194906 A1 | 7/2014 | Topper | |
| 2014/0276975 A1 | 9/2014 | Argentine | |
| 2014/0276979 A1 | 9/2014 | Sauer | |
| 2014/0303654 A1 | 10/2014 | Nobles et al. | |
| 2014/0309670 A1 | 10/2014 | Bakos et al. | |
| 2014/0371790 A1 | 12/2014 | Hatch | |
| 2014/0379006 A1 | 12/2014 | Sutherland et al. | |
| 2015/0100071 A1 | 4/2015 | Phillips et al. | |
| 2015/0126815 A1 | 5/2015 | Nobles | |
| 2015/0196294 A1 | 7/2015 | Murillo | |
| 2015/0313620 A1 | 11/2015 | Suri | |
| 2015/0359531 A1 | 12/2015 | Sauer | |
| 2015/0374351 A1 | 12/2015 | Nobles et al. | |
| 2016/0007998 A1 | 1/2016 | Nobles et al. | |
| 2016/0045315 A1 | 2/2016 | Vola et al. | |
| 2016/0143737 A1 | 5/2016 | Zentgraf | |
| 2016/0151064 A1 | 6/2016 | Nobles | |
| 2016/0324636 A1 | 11/2016 | Rourke | |
| 2016/0345961 A1 | 12/2016 | Sauer | |
| 2017/0035425 A1 | 2/2017 | Fegelman et al. | |
| 2017/0042534 A1 | 2/2017 | Nobles | |
| 2017/0049440 A1 | 2/2017 | Sauer | |
| 2017/0049451 A1 | 2/2017 | Hausen | |
| 2017/0296168 A1 | 4/2017 | Nobles et al. | |
| 2017/0128059 A1 | 5/2017 | Coe et al. | |
| 2017/0245853 A1 | 8/2017 | Nobles | |
| 2017/0303915 A1 | 10/2017 | Nobles | |
| 2018/0311043 A1 | 11/2018 | Neustadter | |
| 2019/0029672 A1 | 1/2019 | Nobles et al. | |
| 2019/0150903 A1 | 5/2019 | Nobles | |
| 2019/0239880 A1 | 8/2019 | Nobles | |
| 2019/0388084 A1 | 12/2019 | Nobles et al. | |
| 2020/0214694 A1 | 7/2020 | Nobles | |
| 2020/0253599 A1 | 8/2020 | Nobles | |
| 2020/0268373 A1 | 8/2020 | Nobles | |
| 2020/0281584 A1 | 9/2020 | Nobles | |
| 2021/0045735 A1 | 2/2021 | Nobles | |
| 2021/0219974 A1 | 7/2021 | Nobles | |
| 2021/0386420 A1 | 12/2021 | Nobles | |
| 2022/0280149 A1 | 9/2022 | Nobles | |
| 2022/0313229 A1 | 10/2022 | Nobles | |

FOREIGN PATENT DOCUMENTS

| | | |
|---|---|---|
| CN | 101257852 | 8/2011 |
| CN | 201280029608.6 | 10/2016 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 1 196 093 | 4/2002 |
| EP | 1 303 218 | 4/2003 |
| EP | 0 941 698 | 5/2005 |
| EP | 0 870 486 | 11/2005 |
| EP | 0 983 027 | 12/2005 |
| EP | 1 852 071 | 11/2007 |
| EP | 1 987 779 | 11/2008 |
| EP | 2 572 649 | 3/2013 |
| EP | 2 413 809 B1 | 10/2014 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 04088978 B2 | 5/2008 |
| JP | 2008-541857 | 11/2008 |
| JP | 2008-546454 | 12/2008 |
| JP | 2009-261960 | 11/2009 |
| JP | 2010-522625 | 7/2010 |
| JP | 2011-067251 | 4/2011 |
| JP | 5848125 | 12/2015 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/25254 | 5/1999 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 09/081396 | 7/2009 |
| WO | WO 11/047201 | 4/2011 |
| WO | WO 11/094619 | 8/2011 |
| WO | WO 11/137224 | 11/2011 |
| WO | WO 11/156782 | 12/2011 |
| WO | WO 12/012336 | 1/2012 |
| WO | WO 13/027209 | 2/2013 |
| WO | WO 13/142487 | 9/2013 |
| WO | WO 15/002815 | 1/2015 |
| WO | WO 15/085145 | 6/2015 |

(56) References Cited

FOREIGN PATENT DOCUMENTS

| WO | WO 17/180092 | 10/2017 |
|---|---|---|
| WO | WO 18/236822 | 12/2018 |
| WO | WO 19/035095 | 2/2019 |
| WO | WO 19/051379 | 3/2019 |
| WO | WO 19/055433 | 3/2019 |

OTHER PUBLICATIONS

Cardio Medical Solutions, Inc. brochure titled: "Baladi Inverter for Clamp less Surgery"—Undated.
Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.
Current Therapy in Vascular Surgery, 2nd edition, by Calvin B. Ernst, M.D. and James C. Stanley, M.D., copyright 1991 By B.C. Decker, Inc., at pp. A and 140.
Eskuri, A., The Design of a Minimally Invasive Vascular Suturing Device, Thesis submitted to Rose-Hulman Institute of Technology, Nov. 1999.
Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.
Nursing the Open-Heart Surgery Patient, By Mary Jo Aspinall, R.N., M.N., copyright 1973 by McGraw Hill, Inc., at pp. 216 and 231.
Operative Arterial Surgery, by P. R. Bell, M.D., and W Barrie, M.D., copyright 1981 by Bell, Barrie, and Leicester Royal Infirmary, printed byJohn Wright &Sons, pp. 16, 17, 104, 105, 112, and 113.
Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.
Techniques in Vascular Surgery, by Denton A. Cooley, MD. and Don C. Wukasch, MD., copyright 1979 by WB. Saunders Co., at pp. 38,57,86,134,156, and 184.
The problem: Closing wounds in deep areas during laparoscopic operations The solution: REMA Medizintechnik GmbH (no date).
Vascular Access, Principles and Practice, 3rd edition, by Samuel Eric Wilson, MD., copyright 1996, 1988,1980 by Mosby-Year Book, Inc., pp. 89 and 159.
Vascular and Endovascular Surgery, by Jonathan D. Beard and Peter Gainers, copyright 1998 by W. B. Saunders Co., Ltd, p. 414.
Vascular Surgery, 3rd edition, vol. 1, by Robert B. Rutherford, MD., copyright 1989, 1984, 1976 By W. B.SaundersCo., at pp. 347, 348, 354, 594, 607, 622, 675, 677, 680, 698, 700, 721, 727, 735, and 829.
Vascular Surgery, 4th edition by Robert B. Rutherford, MD., copyright 1995,1989,1976, by W.B. Saunders Co., vol. 1, at pp. 400-404, 661, and A.
Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.
Vascular Surgery, by Robert B. Rutherford, M.D. copyright1977 by WB. Saunders Co., at pp. 334 and 817.
European Extended Search Report for European Applicaton No. 14867729.7, dated Aug. 25, 2017.
Joshi, Devang J., et al., A Novel Minimal Access Cardiac Surgery Automated Suturing Device with a Needle Sheath to Minimize the Risk of Needle-Stick Injuries, Annual Meeting Posters, IS ISMICS annual scientific meeting, Jun. 3-6, 2015; as available on Jul. 25, 2015 by the Wayback Machine Internet Archive, accessed on Mar. 16, 2022. https://web.archive.org/web/20150625011714/https://meetings.ismics.org/abstracts/2015/P21.cgi.
LSI Solutions, RD180 product device page as available on Mar. 20, 2016 by the Wayback Machine Internet Archive, accessed on Mar. 16, 2022. https://web.archive.org/web/20160320182253/http://www.Isisolutions.com/rd180deviceanatomy.
Ozawa, Soji, et al., (2005). New endoscopic treatments for gastroesophageal reflux disease. Annals of thoracic and cardiovascular surgery: official journal of the Association of Thoracic and Cardiovascular Surgeons of Asia. 11. 146-53.

* cited by examiner

SUTURING METHODS AND APPARATUSES

INCORPORATION BY REFERENCE TO ANY PRIORITY APPLICATIONS

This application is a continuation of U.S. patent application Ser. No. 15/101,607, filed Jun. 3, 2016, titled "SUTURING METHODS AND APPARATUSES," which is a U.S. National Phase of International Patent Application No. PCT/US2014/068742, filed Dec. 5, 2014, titled "SUTURING METHODS AND APPARATUSES,", which claims priority to U.S. Provisional Application No. 61/912,705, filed Dec. 6, 2013, titled "SUTURING METHODS AND APPARATUSES," the entirety of which is incorporated herein by reference.

BACKGROUND

Field

Embodiments of the present disclosure relate to suturing devices and methods. Some embodiments relate to suturing devices and methods for suturing within body lumens.

Description of the Related Art

Health practitioners frequently use sutures for various medical purposes, from closing openings such as natural anatomical openings (including body lumens), cuts, punctures, and incisions in various places in the human body to providing support or structure for repositioning tissue. Generally, sutures are convenient to use and function properly for their desired purpose.

There are some circumstances under which it is not feasible to use conventional sutures and suturing methods to apply a suture. Additionally, there are some circumstances under which the use of conventional sutures and suturing methods are less efficient and/or effective and may subject a patient to risk of infection, delays in recovery, increases in pain, and other complications.

SUMMARY

Embodiments of suturing devices and methods used to apply sutures and/or to suture closed body lumens or openings at, within, or into biological structures are disclosed herein. Various suturing devices and methods can be used to place sutures into body tissue from one side of the tissue, without the need to have a component of the suturing device on an opposite side of the tissue to hold a length of suture, to receive a needle, and/or to provide any other suturing function. This allows for flexibility in available tissue that can be sutured using such a device.

Various suturing devices and methods can be used to place sutures into body tissue from one side of the tissue, without the need to insert components into the tissue beyond needles and the suture itself. This can minimize tissue damage, pain, and/or recovery time.

Various suturing devices and methods can be used for accessing and placing sutures into internal body tissue. Suturing devices described herein allow for quickly and easily applying suture to areas of the body that are often difficult to access with existing suturing devices and methods. The suturing mechanism of these devices can be operated remotely from outside the body, thereby making it possible to perform a wide variety of surgical procedures in a minimally invasive or non-invasive manner. Various suturing devices and methods can be used to select a desired bite size and/or suture depth and apply sutures at the desired bite size and/or suture depth, allowing for even greater flexibility in suturing procedures that can be performed.

One aspect of the disclosure relates to a suturing device for closing an opening in a tubular biological structure having an inner surface, such as, for example, a fallopian tube, a common bile duct, or an arterial-venous fistula. In some embodiments, one or more lengths of suture can be applied through tissue on opposing sides of the inner surface of the tubular biological structure and tightened to pull the opposing sides together.

In various embodiments, a suturing device for applying a suture through body tissue can include an elongate body having a proximal end, a distal end, and a distal-most face defined at least in part by a distal edge of the elongate body. The device can include a handle at the proximal end and a suture holder at the distal end configured to hold a portion suture. The device can also include a needle housed within the elongate body, the needle configured to move outward from within the elongate body through the distal-most face of the elongate body to pass through body tissue and engage the portion of suture held by the suture holder, the needle further being retractable away from the suture holder back through the body tissue to draw the portion of suture through the body tissue.

In various embodiments, a suturing device for applying a suture through body tissue can include an elongate body having a proximal end, a distal end, and a handle at the proximal end. The device can also include a suture holder connected to the elongate body at the distal end and configured to hold a portion of suture. The device can also include a needle housed within the elongate body, the needle configured to move outward from a retracted position within the elongate body to pass through body tissue and engage the portion of suture held by the suture holder, the needle further being retractable away from the suture holder back through the body tissue to draw the portion of suture through the body tissue. In some embodiments, when the needle first moves out of the elongate body the tip of the needle moves in a first direction and when the needle reaches the portion of suture held by the suture holder the tip of the needle is moving in a second direction, the first direction being different from the second direction.

In some embodiments, the tip of the needle can have a velocity component in the distal direction when the needle first moves out of the elongate body, and when the needle reaches the portion of suture held by the suture holder the tip of the needle has a velocity component in the proximal direction.

In some embodiments, the suturing device can further comprise an arm at the distal end of the elongate body, the arm comprising the suture holder and being extendible from the elongate body from a retracted position to an extended position in which the suture holder is a distance away from the elongate body. In some embodiments, the suture holder when the arm is in the extended position can be even with or proximal to the distal-most face of the elongate body. In some embodiments, the needle can be configured to engage the portion of suture held by the suture holder when the arm is in the extended position. In some embodiments, the needle can rotate about an axis of rotation as it moves outward from within the elongate body to engage the portion of suture held by the suture holder. In some embodiments, when the needle engages the portion of suture held by the suture holder, the suture holder can be even with or distal to the axis of rotation. In some embodiments, the needle can maintain substantially the same shape as it moves outward from within the elongate body to engage the portion of suture held by the suture holder. In some embodiments, at least a portion of the needle can be curved.

In some embodiments, the suturing device can further comprise a sheath having a longitudinal axis generally aligned with a longitudinal axis of the elongate body, wherein the sheath is movable relative to the elongate body. In some embodiments, the sheath can be exterior to the elongate body. In some embodiments, at least a portion of the sheath can be configured to be positioned between the tip of the needle in the retracted position and the body tissue to thereby separate the needle a defined distance from the body tissue. In some embodiments, the elongate body can comprise a distal-most face defined at least in part by a distal edge of the elongate body, and the needle moves out of the elongate body by passing through the distal-most face. In some embodiments, the suture holder can be configured to hold the portion of suture on the distal-most face of the elongate body.

In various embodiments, a method of applying suture to an internal biological structure can include delivering a distal end of a suturing device to a position within a patient and adjacent a section of tissue of an internal biological structure; advancing a needle into the section of tissue in a first direction; advancing the needle in a second direction different from the first direction and into engagement with a suture portion; retracting the needle back through the section of tissue to draw the suture portion through the section of tissue; and withdrawing the distal end of the suturing device from the position adjacent the section of tissue to be sutured.

In some embodiments, the needle can be advanced into the section of tissue from a first side of the tissue and the needle passes out of the section of tissue through the first side of the tissue before engaging with the suture portion. In some embodiments, advancing the needle in the first direction and advancing the needle in the second direction can be a continuous advancement. In some embodiments, advancing the needle can comprise rotating the needle. In some embodiments, the method can further comprise positioning a distal-most face of an elongate body of the suturing device adjacent the section of tissue prior to advancing the needle. In some embodiments, the method can further comprise advancing a sheath distal to the elongate body to separate the distal-most face of the elongate body from the section of tissue.

In some embodiments, the distal-most face of the elongate body can be positioned flush against the section of tissue. In some embodiments, advancing the needle into the section of tissue can comprise advancing the needle from a retracted position within the suturing device through a distal-most face of the suturing device.

In various embodiments, a method of suturing an internal body lumen can include delivering a distal end of a suturing device for placing a first suture into a body lumen; aligning the distal end of the suturing device with an inner wall of the body lumen at a first entry location; advancing a needle of the suturing device through the inner wall in a first direction at the first entry location; advancing the needle of the suturing device in a second direction different from the first direction and into engagement with a first suture portion; retracting the needle of the suturing device back through the first entry location to draw the first suture portion through the inner wall; withdrawing the distal end of the suturing device from alignment with the inner wall at the first entry location. The method can also include aligning a distal end of a suturing device for placing a second suture with the inner wall of the body lumen at a second entry location on an opposite side of the body lumen as the first entry location; advancing a needle of the suturing device for placing a second suture through the inner wall in a third direction at the second entry location; advancing the needle of the suturing device for placing a second suture in a fourth direction different from the third direction and into engagement with a second suture portion; retracting the needle of the suturing device for placing a second suture back through the second entry location to draw the second suture portion through the inner wall; withdrawing the distal end of the suturing device for placing a second suture from alignment with the inner wall at the second entry location; and drawing the portion of the first suture through the inner wall closer to the portion of the second suture through the inner wall to thereby tighten the body lumen.

In some embodiments, the suturing device for placing a first suture and the suturing device for placing a second suture can be the same suturing device. In some embodiments, the first suture can be joined with the second suture before the portion of the first suture through the inner wall is drawn closer to the portion of the second suture through the inner wall. In some embodiments, the method can further comprise withdrawing the suturing device for placing a first suture prior to aligning a distal end of a suturing device for placing a second suture. In some embodiments, the first suture portion can be within the body lumen when the needle of the suturing device for placing a first suture engages the first suture portion. In some embodiments, the method can further comprise advancing the needle of the suturing device for placing a first suture through the inner wall and into the body lumen at a first exit location different from the first entry location.

In various embodiments, a suturing device for applying a suture through body tissue can include an elongate body having a proximal end, a distal end, and a handle at the proximal end, a suture holder connected to the elongate body at the distal end and configured to hold a portion of suture, and a curved needle housed within the elongate body, the needle configured to rotatably move outward from a retracted position within the elongate body to pass through body tissue and engage the portion of suture held by the suture holder, the needle further being rotatably retractable away from the suture holder back through the body tissue to draw the portion of suture through the body tissue, wherein the needle rotates about an axis of rotation as it moves outward from within the elongate body to engage the portion of suture held by the suture holder.

DETAILED DESCRIPTION

Embodiments of suturing devices and methods which can be used to apply sutures to internal biological structures and internal body tissue are described herein. The suturing devices and methods can be used to place sutures from one side of a biological structure or tissue without the need to position a component of the device on a second side of a biological structure or tissue, and without the need to puncture the tissue with anything beyond a needle. This can increase the number of possible suture sites and minimize tissue damage, pain, and/or recovery time, among other advantages.

In the embodiments described herein, the disclosed devices can be used to place sutures in a variety of body locations. For example, in some embodiments, the disclosed suturing devices and methods are well-suited for passing suture through the wall of a tubular biological structure from a location within the lumen or around the ostium for the purpose of closing the tubular biological structure. In some embodiments, the suturing devices and methods can be used for tubal sterilization. In some embodiments, they can be used for procedures such as a vasectomy, treatment of bladders, or uterine prolapse. In some embodiments, the suturing devices and methods can be used to apply internal sutures to control and/or adjust positioning of breast implants, such as by applying skin grafts.

In some embodiments, the suturing devices can be used to close or reduce a variety of tissue openings, lumens, hollow organs, or natural or surgically created passageways in the body. In some embodiments, the suturing devices can be used to suture prosthetics, synthetic materials, or implantable devices in the body. For example, the devices can be used to suture a pledget within the body.

Suturing devices described herein can be delivered to a suturing site through a variety of methods. In some embodiments, a suturing device can be configured to follow a guide wire to a suturing site. In some embodiments, a delivery sheath can be inserted into a patient's body and a suturing device can be passed through the delivery sheath to the suturing site.

Figure 1:
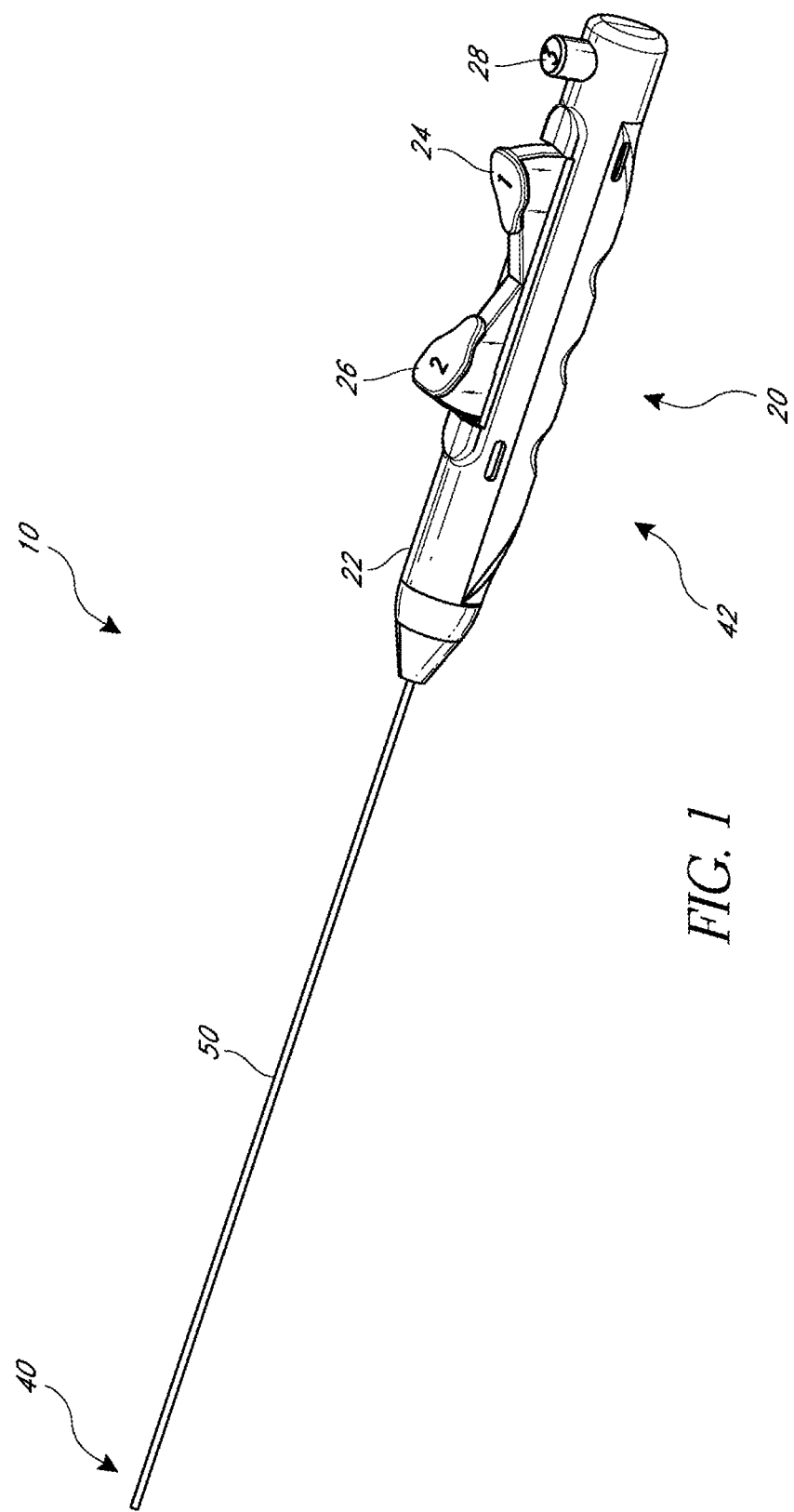
FIG. 1 is a perspective view of an embodiment of a suturing device.

FIG. 1 illustrates one embodiment of a suturing device 10 that can be used to suture body tissue of a patient. The suturing device 10 can have a distal end 40 and a proximal end 42. It can include an elongate body 50 and, in some embodiments, can include a handle portion 20. In some embodiments, the handle portion 20 can include a housing 22 and one or more buttons, levers, or other actuating members such as a first button 24, a second button 26, and/or a third button 28. In various embodiments, different buttons can be used to actuate different components of the suturing device 10, as described in more detail below. Further details regarding handles and associated components are provided in U.S. Patent Publication No. 2008/0269786, published on Oct. 30, 2008, and U.S. Pat. No. 7,803,167, issued on Sep. 28, 2010, the contents of both of which are hereby incorporated by reference herein in their entirety.

Figure 2:
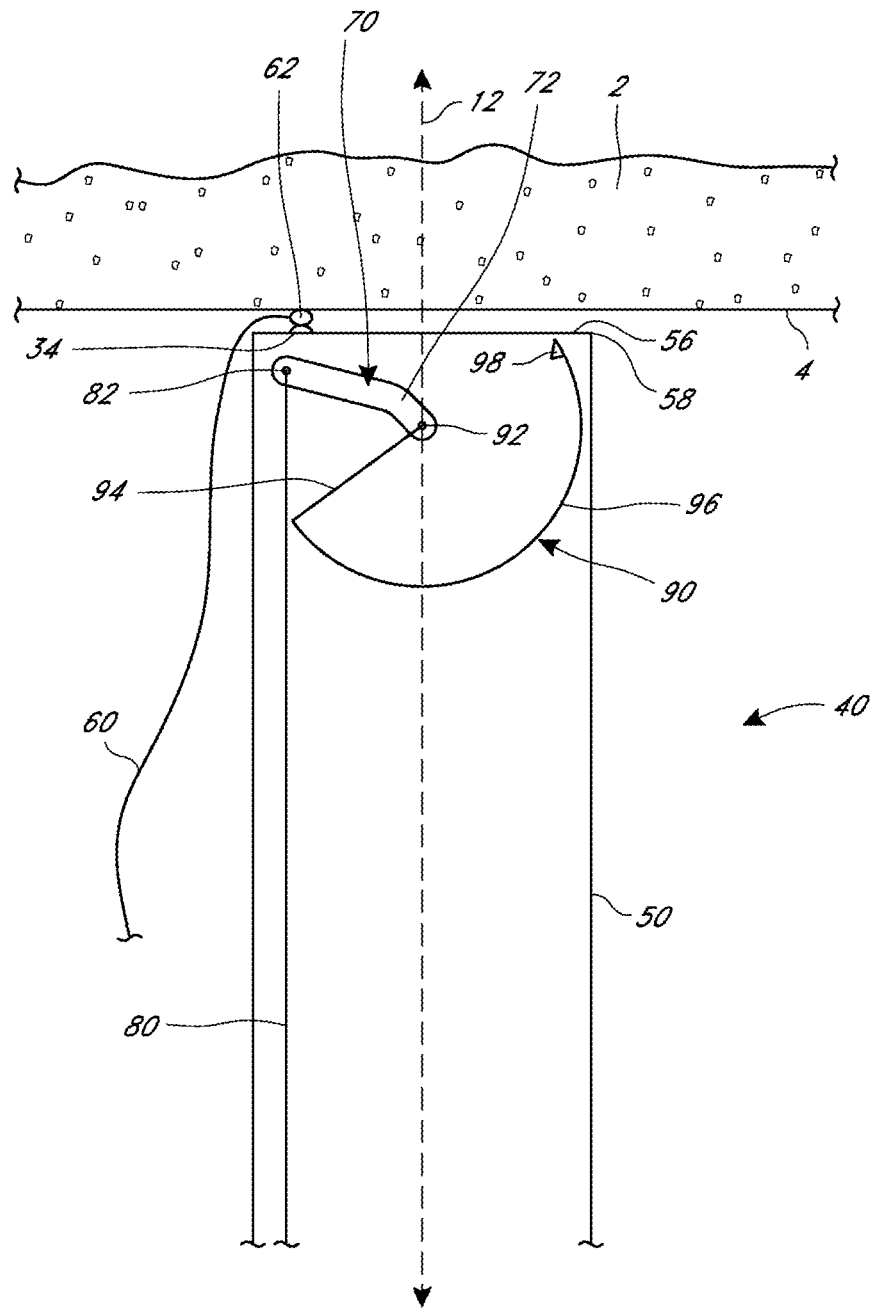
FIG. 2 is a schematic cross-sectional view of a distal end of an embodiment of a suturing device.

FIG. 2 illustrates a schematic cross-sectional view of a distal end 40 of one embodiment of a suturing device. The elongate body 50 of the suturing device can have a distal-most face 56 that can be defined, at least in part, by a distal edge 58. In some embodiments, the distal face 56 can be left open or can be at least partially covered. In some embodiments, when the device is in use the distal face 56 can be positioned adjacent to or in contact with a tissue wall 4 of a body tissue 2 that is to be sutured.

In some embodiments, the suturing device can include a suture catch mechanism or needle 90. The needle 90 can be configured to move from a retracted position, in which the needle is partially or completely within the elongate body, to an extended position in which the needle 90 moves at least partially out from the elongate body 50. In some embodiments, the needle 90 can move into the extended position by passing through the distal-most face 56 of the elongate body 50. In some embodiments, the needle 90 can exit the elongate body 50 by passing through other faces. In some embodiments, the needle 90 can pass through a surface at the distal-most face 56.

The needle 90 can have a variety of configurations. In some embodiments, as illustrated in FIG. 2, the needle can have a tip 98 configured to engage a suture portion, as described below. In some embodiments, the tip 98 can be sharp to pierce tissue. In some embodiments, the needle 90 can have a curved section 96 and/or a lever section 94. In some embodiments, the needle 90 can be configured to rotate about a pivot point 92 that can define an axis of rotation for the needle.

The needle 90 can attach to a needle driver 70 that can drive the needle 90 from and to its retracted position. The needle 90 and needle driver 70 can attach to each other at the pivot point 92. The needle 90 and needle driver 70 can be fixed relative to each other. In some embodiments, the pivot point 92 can define an axis of rotation for both the needle 90 and the needle driver 70. In some embodiments, the needle driver 70 and needle 90 can fixedly connect to each other at a location that differs from an axis of rotation of the needle 90 and the needle driver 70.

In some embodiments, an actuator or push rod 80 can connect to the needle driver 70 at a connection point 82. The actuator or push rod 80 can be connected to a handle of the suturing device, and activating various buttons, levers, or other devices in the handle can cause the push rod 80 to move distally or proximally within the elongate body 50. In the illustrated embodiment, moving the push rod 80 proximally will provide a force on the needle driver 70 through the connection point 82. This force can cause the needle driver 70 to rotate about an axis of rotation, such as at the connection point 92, causing the needle 90 to rotate as well. When the needle driver 70 rotates, it can move the needle 90 from a retracted position, such as the position shown in FIG. 2, to an extended position, such as the position shown in FIG. 3. Preferably, the connection point 82 between the actuator 80 and the needle driver 70 can have at least one degree of freedom, such as by allowing relative rotation between the needle driver 70 and the actuator rod 80. In some embodiments, when the actuator rod 80 moves proximally or distally it can also move laterally, as illustrated.

Figure 3:
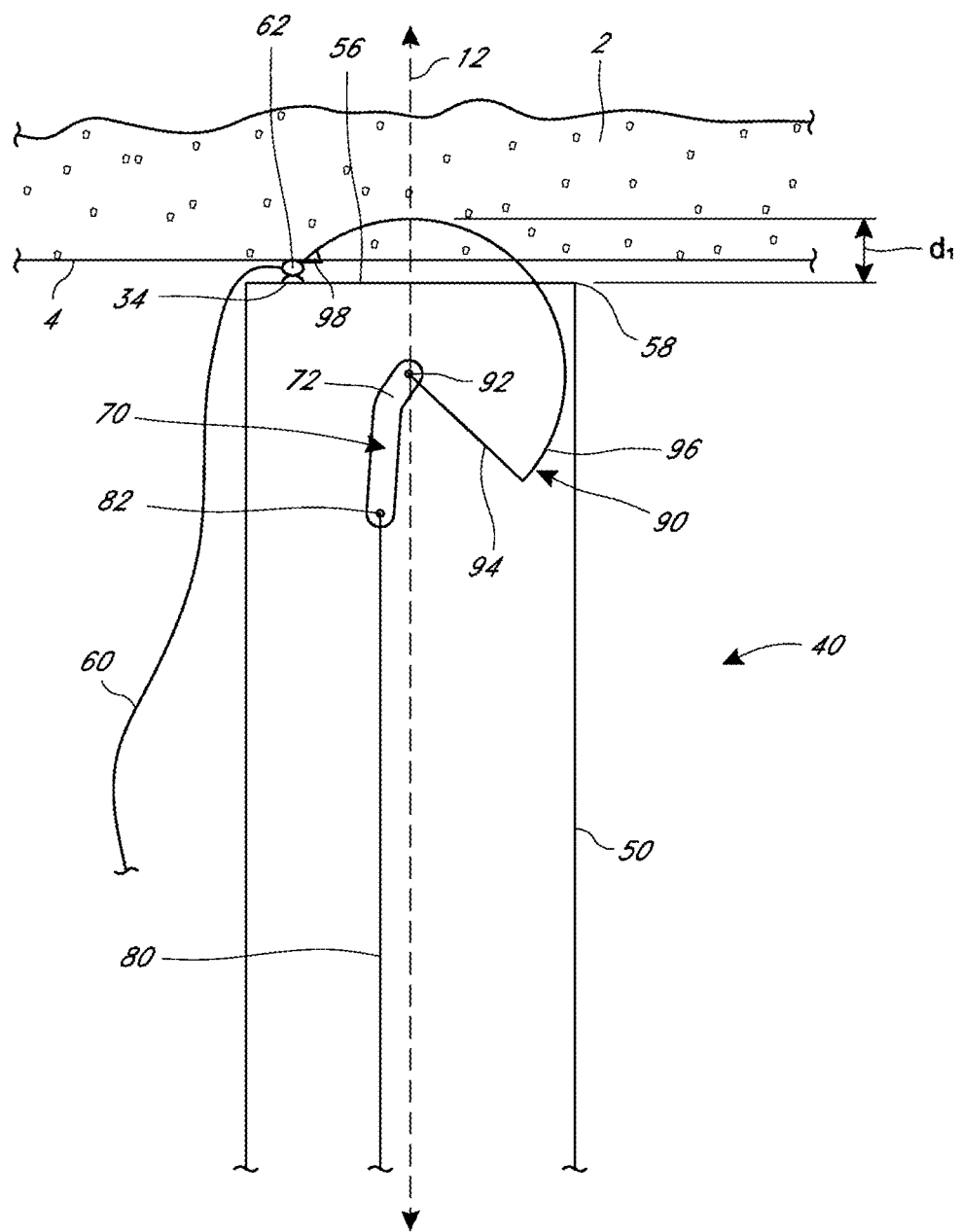
FIG. 3 is a schematic cross-sectional view of a distal end of the suturing device of FIG. 2.

As shown in FIG. 3, as the needle 90 moves from the retracted position, the tip 98 of the needle 90 can leave the elongate body 50 by exiting through the distal face 56 of the elongate body. The needle 90 can then pass through the tissue wall 4 and into the body tissue 2. In some embodiments, the needle tip 98 can have a velocity when it first leaves the elongate body that differs from the velocity of the tip 98 when it reaches a portion of suture 60, described below. In some embodiments, the needle tip 98 can have a distal velocity component as the needle 90 first leaves the elongate body 50. As the needle 90 rotates, however, the tip 98 can turn and develop a proximal velocity component. The path of rotation can cause the needle 90 to turn and exit the tissue 2, passing through the tissue wall 4 a second time and at a location different from where it first passes through the tissue wall 4. In some embodiments, the needle 90 can exit the tissue 2 at the same location where it first passes through the tissue wall 4.

In some embodiments, the suturing device can include a suture holder or clasp 34 configured to be positioned in alignment with the path of the needle 90 when it exits the tissue 2. The suture holder or clasp 34 can be configured to releasably retain a capture portion 62 of suture 60 that is configured to be captured by the needle 90. In various embodiments, the capture portion can be a loop 62, sphere, ferrule, donut, or other configuration. In various embodiments, the suture holder or clasp 34 can include a circular opening with a diameter sized to securely receive and hold the capture portion. Further details regarding suture clasps are provided in U.S. Patent Publication No. 2008/0269786, the entirety of which is hereby incorporated by reference. In some embodiments, the suture holder or clasp 34 can be connected to the elongate body 50.

In various embodiments, the suture holder 34, capture portion 62, and suture 60 can be positioned at different locations. For example, as illustrated, in some embodiments the capture portion 62 can be on or adjacent the distal face 56. In some embodiments, the capture portion and suture holder 34 can be positioned proximal to the distal face 56 (e.g., within the elongate body 50). In some embodiments, the capture portion and suture holder 34 can be positioned distal to the distal face 56. In some embodiments, the capture portion and suture holder 34 can be positioned lateral to the distal face 56. In some embodiments, the capture portion and suture holder 34 can be configured to be positioned within or partially within the body tissue, such that a needle 90 can engage the capture portion 34 without exiting the tissue 2. The length of suture 60 is illustrated as passing outside of the elongate body 50, but in some embodiments the suture 60 can run within the elongate body to a position outside of a patient and/or outside of the suturing device.

Once the needle 90 has engaged the suture 60 at the capture portion 62, the needle 90 can be withdrawn back through the body tissue 2 and into the elongate body 50, bringing a portion of suture 80 with it. The needle 90 can be withdrawn by moving the actuator 80 distally, which can cause the needle driver 70 to rotate back towards its position in FIG. 2, drawing the needle 90 back towards its position in FIG. 2 as well. In some embodiments, a suturing device can be configured such that moving the actuator 80 in a distal direction drives the needle 90 from the retracted to extended position, and moving the actuator 80 in a proximal direction drives the needle 90 from an extended position to the retracted position.

In some embodiments, the needle 90 can be shaped in order pass a defined maximum distance or depth $d_1$ from the elongate body. In some embodiments, where the distal-most face 56 of the elongate body is positioned flush against a tissue wall 4, the depth $d_1$ can be approximately equal to the depth that the needle 90 passes through the tissue 2. In some embodiments, the elongate body 50 can be positioned a distance away from the tissue wall 4 in view of the maximum distance $d_1$ to thereby adjust the depth that a needle 90 passes into the tissue 2 to a desired value. Various configurations to allow for setting this distance are described further below.

The needle driver 70 can be sized and positioned in different locations to affect the operation of a suturing apparatus. In some embodiments, for example, the needle driver 70 can have one or more bent or angled sections 72. This can affect the rotation of the needle driver 70 and the amount of space that it takes up within the elongate body 50. In some embodiments, the needle driver 70 can be positioned such that the pivot point 92 that defines an axis of rotation of the needle 90 is on a central longitudinal axis 12 of the elongate body 50. In some embodiments, the pivot point 92 can be positioned to one side or another of the central longitudinal axis 12.

In some embodiments, the needle driver 70 can be positioned such that the pivot point 92 that defines an axis of rotation of the needle 90 is proximal to the capture portion 62 of suture. In some embodiments, the needle driver 70 can be positioned such that the pivot point 92 that defines an axis of rotation of the needle 90 is in alignment with or distal to the capture portion 62 of suture.

As discussed above, the suturing device can be configured such that moving the actuator or push rod 80 in a proximal or distal direction will cause the needle driver 70 to move the needle 90 from a retracted position to an extended position. In some embodiments, the device is configured such that the push rod 80 can move either proximally or distally to move the needle 90 all the way into engagement with the suture portion 60. For example, in the illustrated embodiment, the connection 82 between the needle driver 70 and the actuator 80 can remain on the same side of the pivot point 92 through the range of motion of the needle 90 between the retracted and extended positions. Thus, a proximal force at the connection point 82 can be sufficient to move the needle 90 from the retracted to the extended position, and a distal force at the connection point can be sufficient to move the needle 90 from the extended to the retracted position. At least a portion of the actuator or push rod 80, however, can move laterally as the needle driver 70 rotates.

In various embodiments, the suture capture portion 62 can be positioned at different locations relative to the elongate body 50. As described above, for example, in some embodiments, the capture portion 34 can be positioned between a distal-most face 56 of the elongate body and tissue wall 4. In some embodiments, as illustrated in FIGS. 4 and 5, the suture loop 62 can be positioned at other locations.

Figure 4:
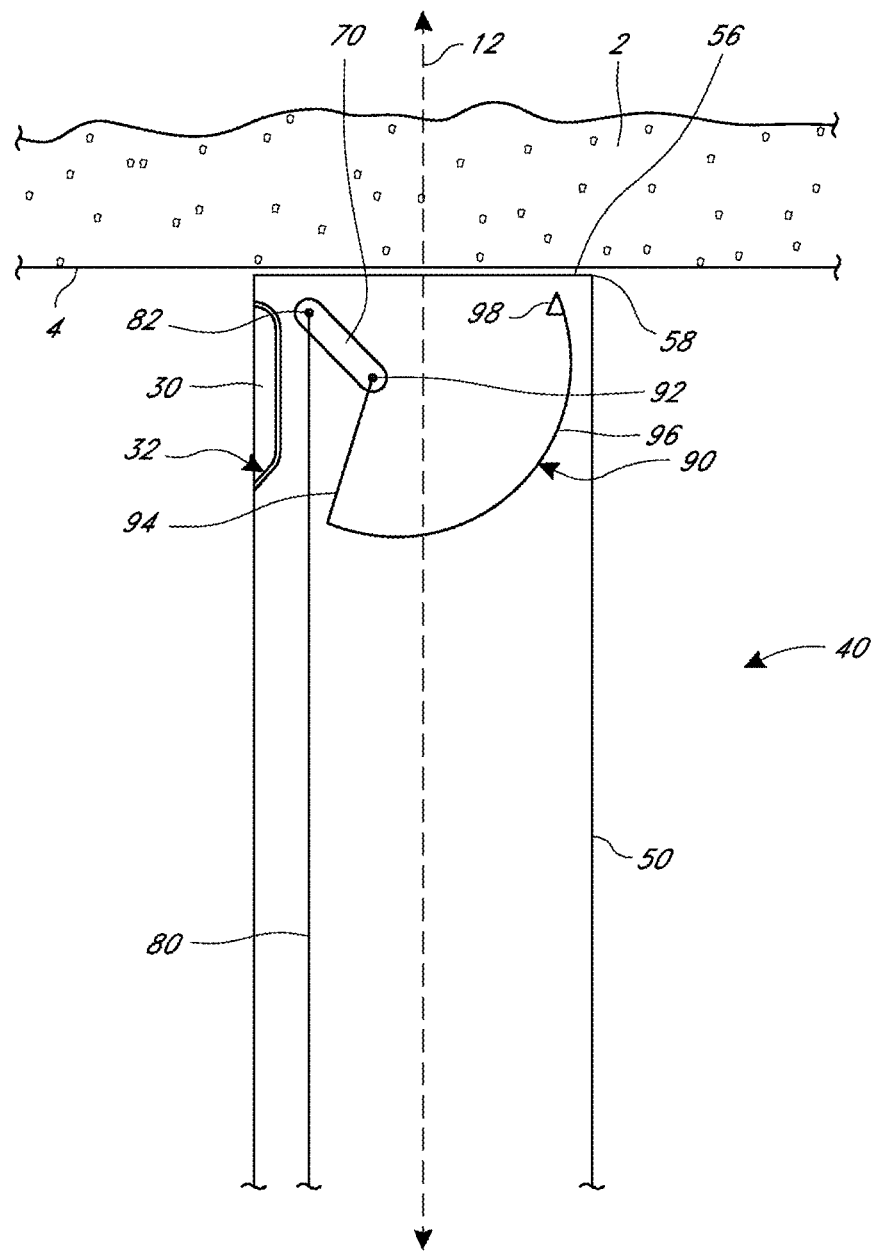
FIG. 4 is a schematic cross-sectional view of a distal end of an embodiment of a suturing device.
Figure 5:
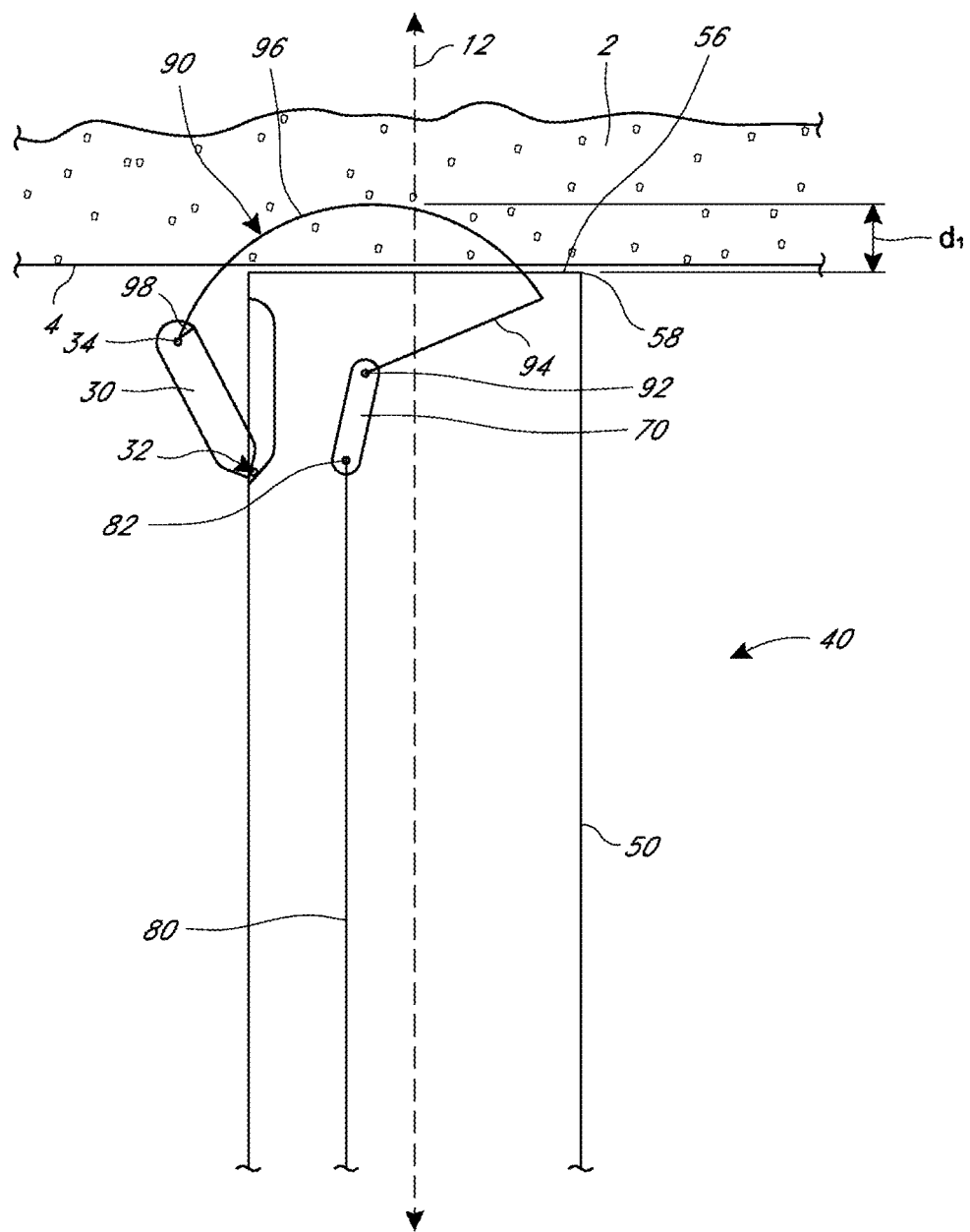
FIG. 5 is a schematic cross-sectional view of a distal end of the suturing device of FIG. 4.

FIGS. 4 and 5 illustrate one embodiment of a suturing device that includes a suture arm 30. In FIG. 4, the suture arm 30 is in a retracted position in which at least a portion of the suture arm 30 is within the elongate body 50. In some embodiments, the entirety of the suture arm 30 can be within the elongate body 50 when the suture arm 30 is in the retracted position. The suture arm 30 can include a pivot 32 about which the suture arm 30 can move from the retracted to an extended position, illustrated in FIG. 5. In some embodiments, the pivot 32 can be at a proximal end of the suture arm 30 and the suture arm 30 can point distally, as illustrated, and in some embodiments, the pivot 32 can be at a distal end of the suture arm 30 and the suture arm 30 can point proximally. In some embodiments, the suture arm 30 can translate (such as by sliding, though other means can be used as well) from the retracted to extended position in addition to or instead of pivoting. In some embodiments, at least a portion of the suture arm 30 can be distal to the distal face 56 when in the extended position. In some embodiments, at least a portion of the suture arm 30 can be configured to pass through a tissue wall 4 when in the extended position.

In some embodiments, the suture arm 30 can include a suture clasp 34, which can be configured to releasably retain a capture portion 62 of a suture (not illustrated), such as a suture loop, donut, sphere, ferrule, etc. The needle 90 and needle driver 70 can be sized and configured such that the needle 90 in the extended position, as illustrated in FIG. 5, engages a capture portion of a suture releasably held by a suture clasp 34. The needle 90 can then draw the suture back through the body issue 2 as it returns to a retracted position, as illustrated in FIG. 4.

FIGS. 4 and 5 also illustrate an embodiment of a suturing device that has a needle driver 70 positioned such that the pivot point 92 and axis of rotation of the needle driver 70 and the needle 90 are offset from a central longitudinal axis 12 of the suturing device. FIGS. 4 and 5 also illustrate an embodiment of a suturing device in which the needle driver 70 is generally straight and does not have a bend 72.

In some embodiments, it can be desirable to modify the depth that the needle 90 passes into body tissue 92. In some embodiments, this can be done by using a device or component that can be configured to separate the elongate body from a tissue wall 4, which can lessen the distance that the needle 90 will pass into the body tissue 2. Preferably, the device or component can separate the elongate body from the tissue wall by a known, desired amount. In some embodiments, the elongate body can move relative to the needle driver 70 and needle 90, such that when the elongate body is positioned against the tissue wall 4, the pivot point 92 and axis of rotation of the needle can be farther from or closer to the tissue wall, thereby adjusting the depth that the needle can pass into body tissue.

Figure 6:
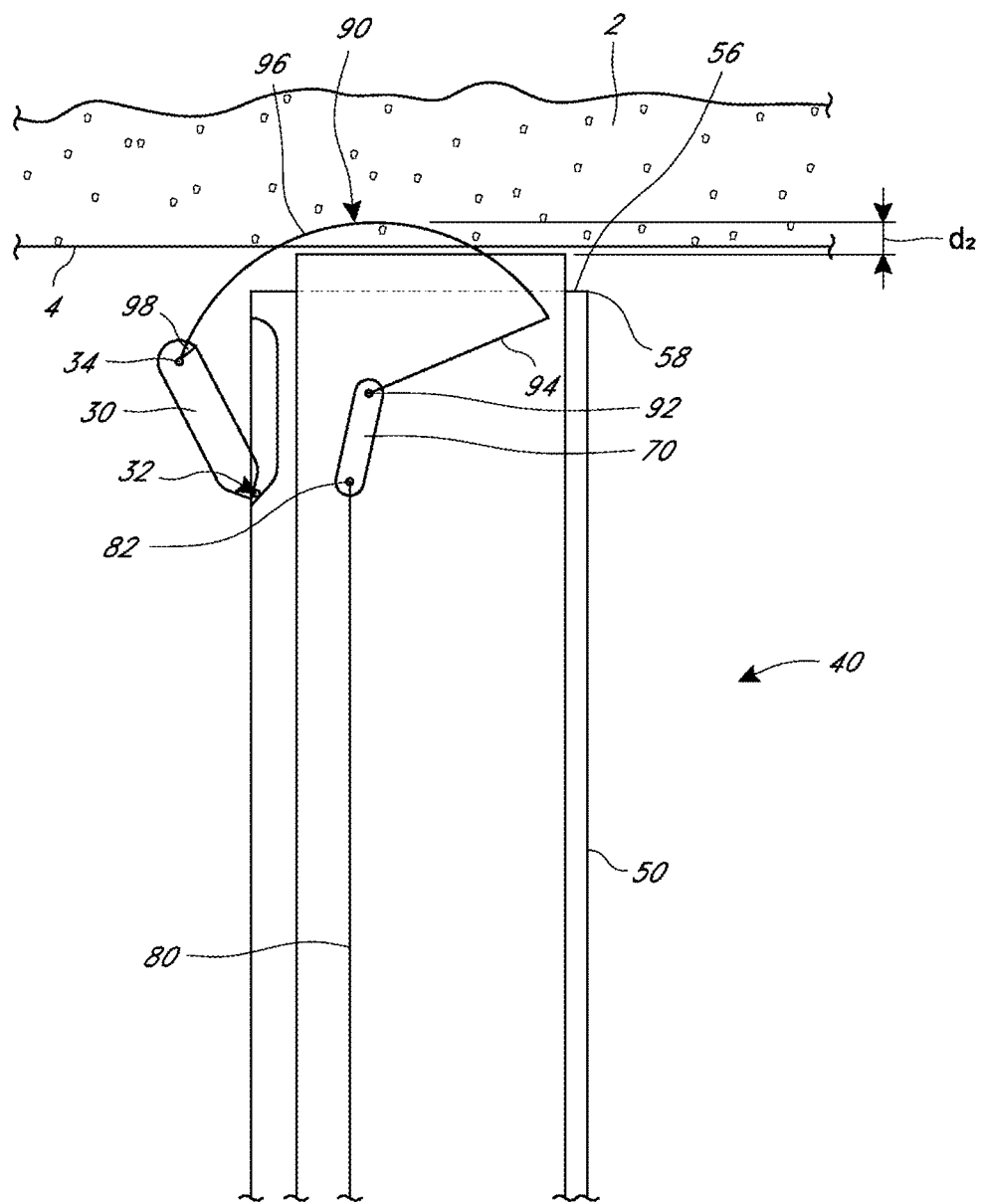
FIG. 6 is a schematic cross-sectional view of a distal end of an embodiment of a suturing device that includes a sheath.

In some embodiments, as illustrated in FIG. 6, an interior sheath 54 can be positioned within the elongate body 50 and can be independently movable within and relative to the elongate body 50. The sheath 54 can preferably be controlled from a proximal end of the suturing device, such as at the handle. In some embodiments, the suturing device can have a known maximum depth $d_1$, as described and illustrated above. In some embodiments, the sheath 54 can be figured to protrude from a distal-most face 56 of the elongate body a known amount. When using the suturing device, the sheath 54 can be positioned adjacent to or against the tissue wall 4, which separates the distal-most face 56 of the elongate body 50 from the tissue wall 4 by that known amount. The depth of the needle $d_2$ through the tissue is therefore the maximum depth $d_1$ of the device less the known amount that the sheath 54 extends from the elongate body 50. Adjusting the position of the sheath 54 relative to the elongate body 50 therefore also adjusts the depth $d_2$ that the needle 90 passes through tissue.

In some embodiments, the proximal end of the suturing device can include mechanisms to maintain the sheath 54 in a desired position. For example, in some embodiments the sheath 54 and a portion of the proximal end of the device, such as the handle, can have mating detents at discrete distance intervals. In some embodiments, the sheath 54 can be engaged relative to the elongate body 50 (e.g., with threading), such that rotating the sheath 54 relative to the elongate body advances or retracts the sheath 54. Different relative distances can be labeled at the proximal end of the device such that an operator can identify how far the sheath 54 extends from the elongate body 50.

Figure 7:
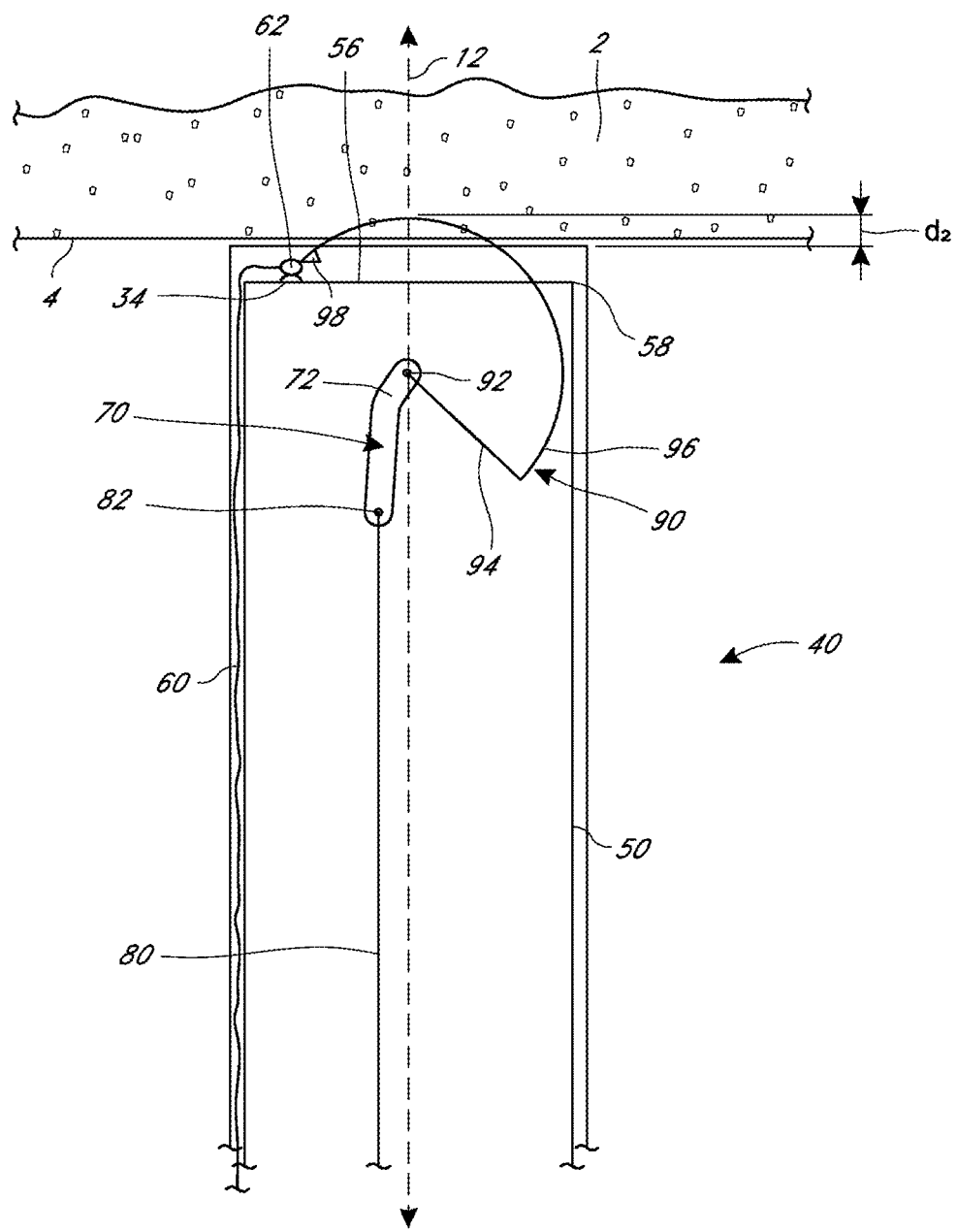
FIG. 7 is a schematic cross-sectional view of a distal end of an embodiment of a suturing device that includes a sheath.

FIG. 6 illustrates the use of the sheath 54 with an embodiment of a suturing device that includes a suture arm 30, but the sheaths described herein are not limited to any particular embodiment and can be applied to any of the embodiments described herein. For example, FIG. 7 illustrates an embodiment of a suturing device that includes a sheath used with a suturing device that does not have a suture arm and that has the suture capture portion 62 positioned on or near the distal-most face 56 of the elongate body. In some embodiments, as further illustrated, a sheath can be an exterior sheath 55 that can be positioned at least partially around the elongate body 50. As above, the positioning of the sheath 55 can be adjusted from a proximal end of the suturing device. The sheath 55 can be used to separate the distal-most face 56 of the elongate body varying distances from a tissue wall 4 to thereby modify the depth $d_2$ that the needle 90 passes through tissue 2.

In some embodiments, a suturing device can be delivered through an introducer sheath to a portion of tissue 2 needing to be sutured. In some embodiments, the introducer sheath can be configured to operate as a sheath used to separate the elongate body 50 from a tissue wall 4. In some embodiments, different sheaths can be used. In some embodiments, where an exterior sheath 55 is used to adjust the depth $d_2$, the length of suture 60 can run between the elongate body 50 and the exterior sheath 55. In some embodiments, the suture 60 may run outside of both the elongate body and an exterior sheath 55. In some embodiments, the suture 60 may run inside or outside of an introducer sheath 55.

Figure 8:
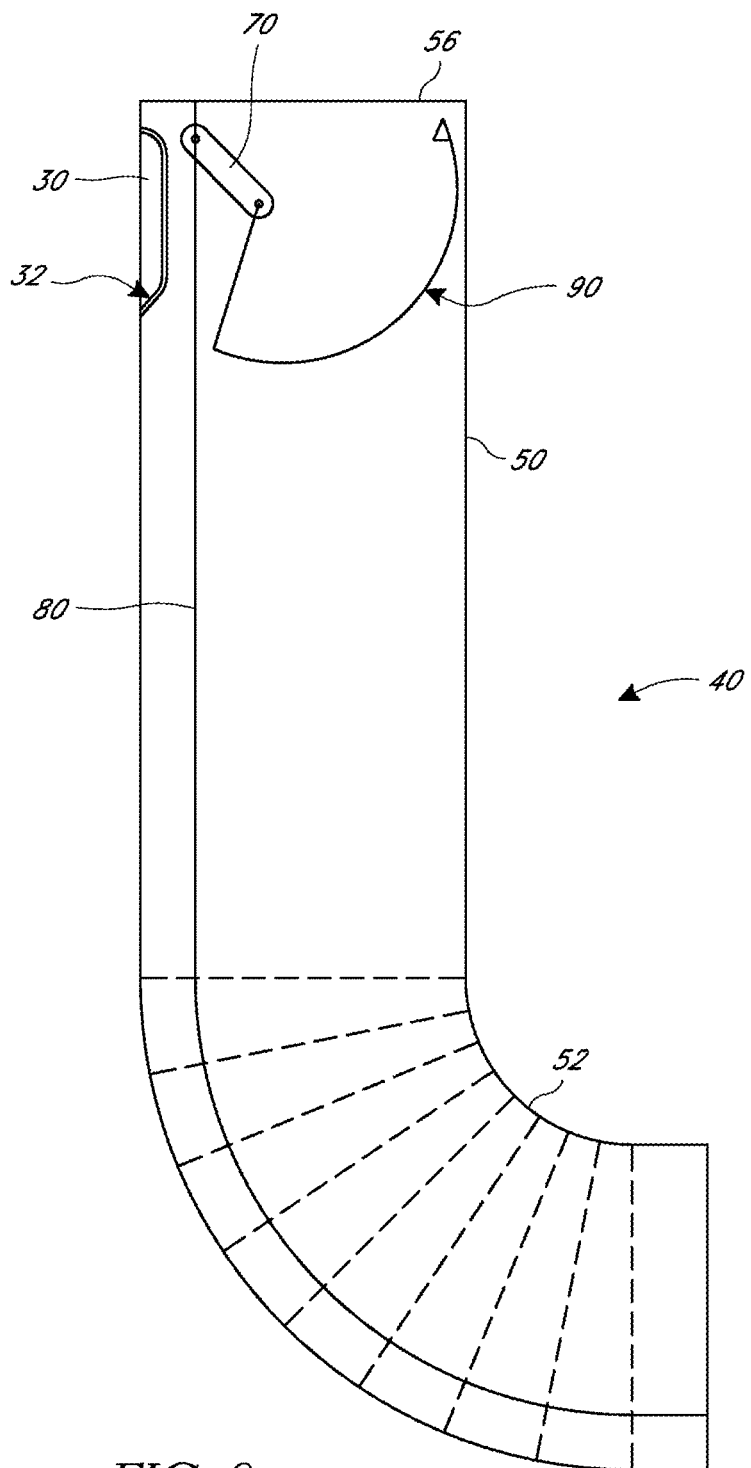
FIG. 8 is a schematic cross-sectional view of a distal end of an embodiment of a suturing device that can articulate.

In various embodiments, a suturing device may be desirable for use at locations in a body that are not easily accessed or that have tight corners. In some embodiments, as illustrated in FIG. 8, the elongate body 50 of a suturing device can have one or more articulated sections 52 that can allow the elongate body to bend. This can help fit the elongate body 50 into a desired location and/or align a distal-most face 56 of the elongate body with tissue desired to be sutured. For example, in some embodiments the articulated sections 52 can allow the elongate body 50 to bend 30, 45, 90, 180, or 360°. Further, in some embodiments the articulated sections 52 can be manually articulated from the handle or may be articulated by the body.

Figure 9:
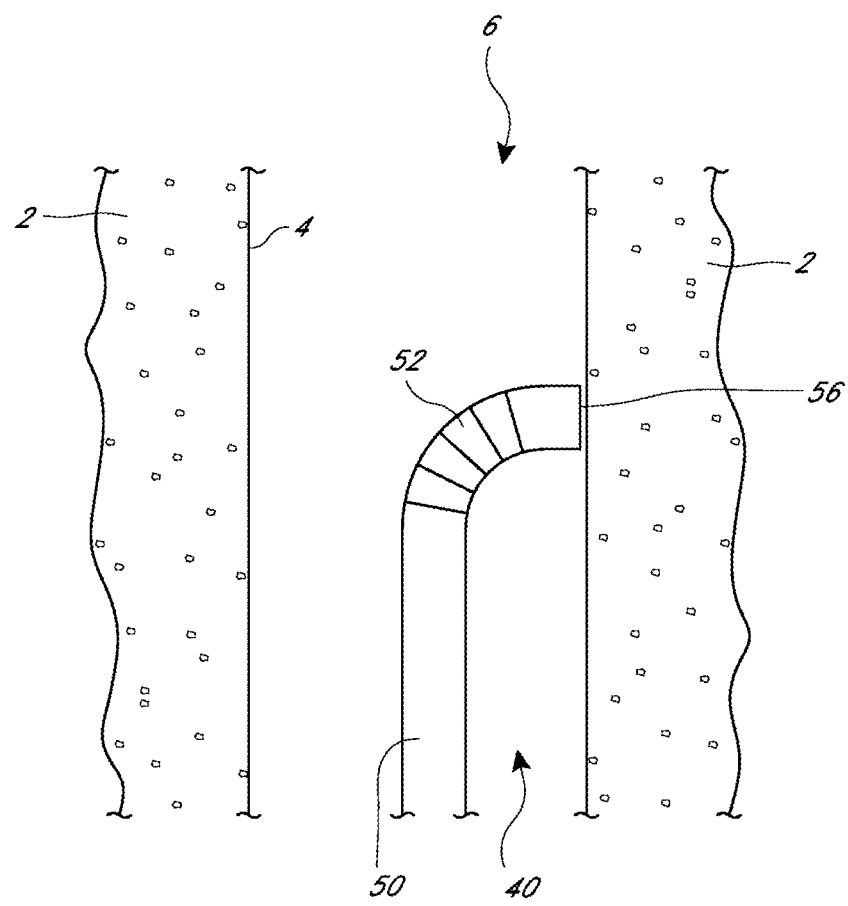
FIG. 9 is a schematic view of an embodiment of a suturing device in a body lumen.

FIGS. 9-16 illustrate one embodiment of a method of using a suturing device to place suture in tissue surrounding a body lumen 6 in order to constrict or close the body lumen. As illustrated in FIG. 9, a distal end 40 of the elongate body 50 of the suturing device can be delivered within the body lumen 6, and the distal-most face 56 of the elongate body can be positioned adjacent, or directly on, the tissue wall 4 of the body tissue 2 desired to be sutured. In some embodiments, an articulated section 52 can be used to align the distal face 56 with the tissue wall 4. In some embodiments, the elongate body 50 can be directly aligned with a tissue wall 4 without articulating or as a result of a natural flexibility of the elongate body 50.

Figure 10:
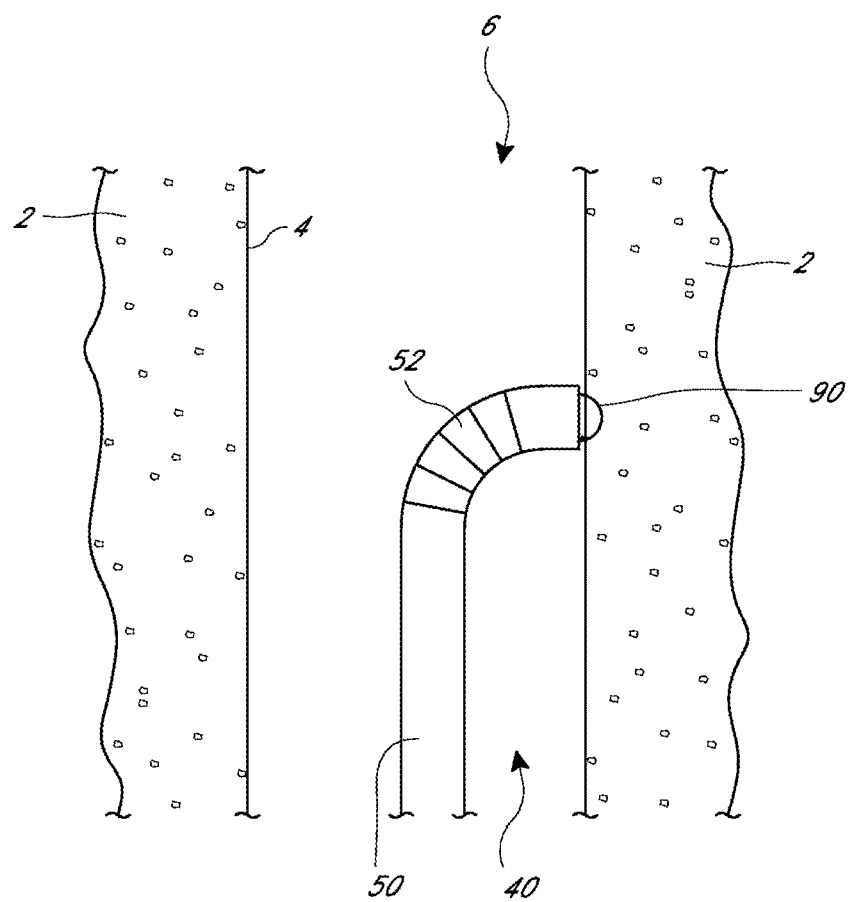
FIG. 10 is a schematic view as in FIG. 9 showing a needle in an extended position.
Figure 11:
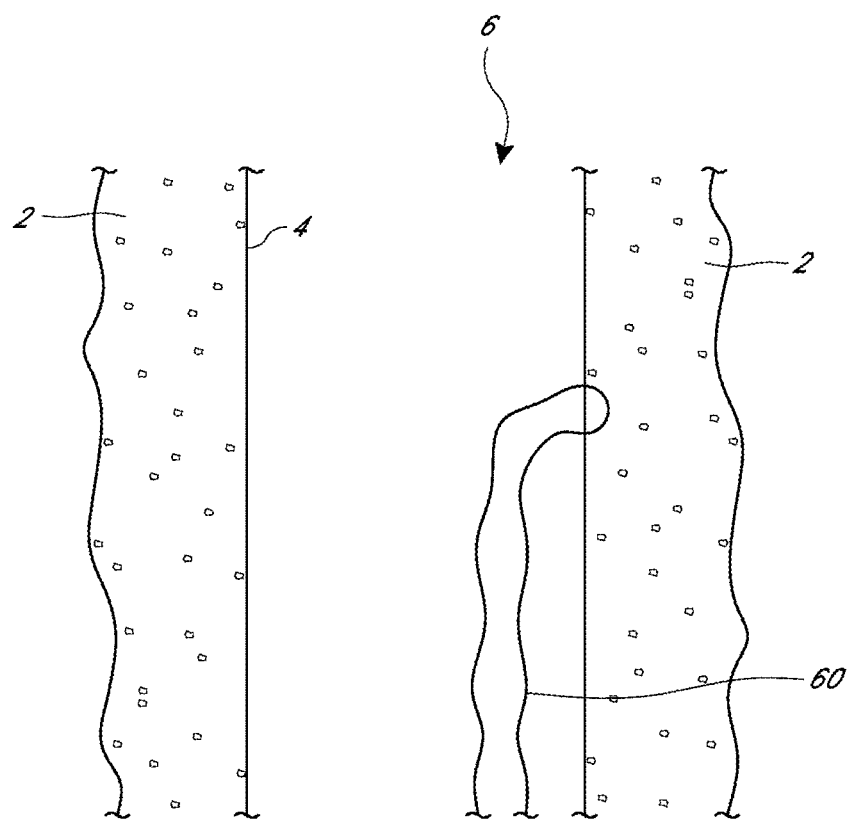
FIG. 11 is a schematic view as in FIG. 10 showing a length of suture running through body tissue.

As illustrated in FIG. 10, a needle 90 can be extended as described above and can pass through a portion of the body tissue 2 in order to engage a suture portion (not illustrated). The needle 90 can be retracted to draw the suture portion through the tissue, also as described above, and into the elongate body 50. The elongate body can be withdrawn, as illustrated in FIG. 11, leaving a suture portion 60 through the body tissue 2.

Figure 12:
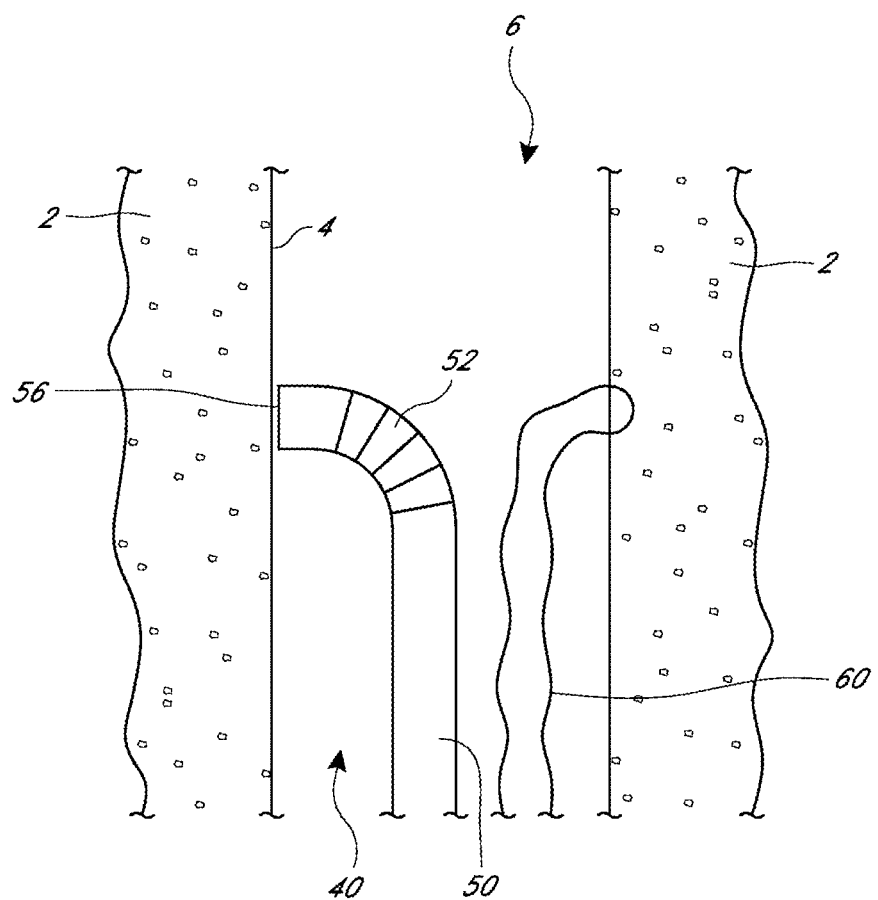
FIG. 12 is a schematic view as in FIG. 11 showing an embodiment of a suturing device in the body lumen.

FIG. 12 illustrates a suturing device positioned to pass sutures through a tissue wall 4 generally opposite the tissue wall that contains the suture portion 60. In some embodiments, a second suturing device can be used. In some embodiments, the suturing device used can be the same suturing device used to place the suture portion 60. In some embodiments, when the same suturing device is used, a device with multiple needles and/or suture portions can be used.

Figure 13:
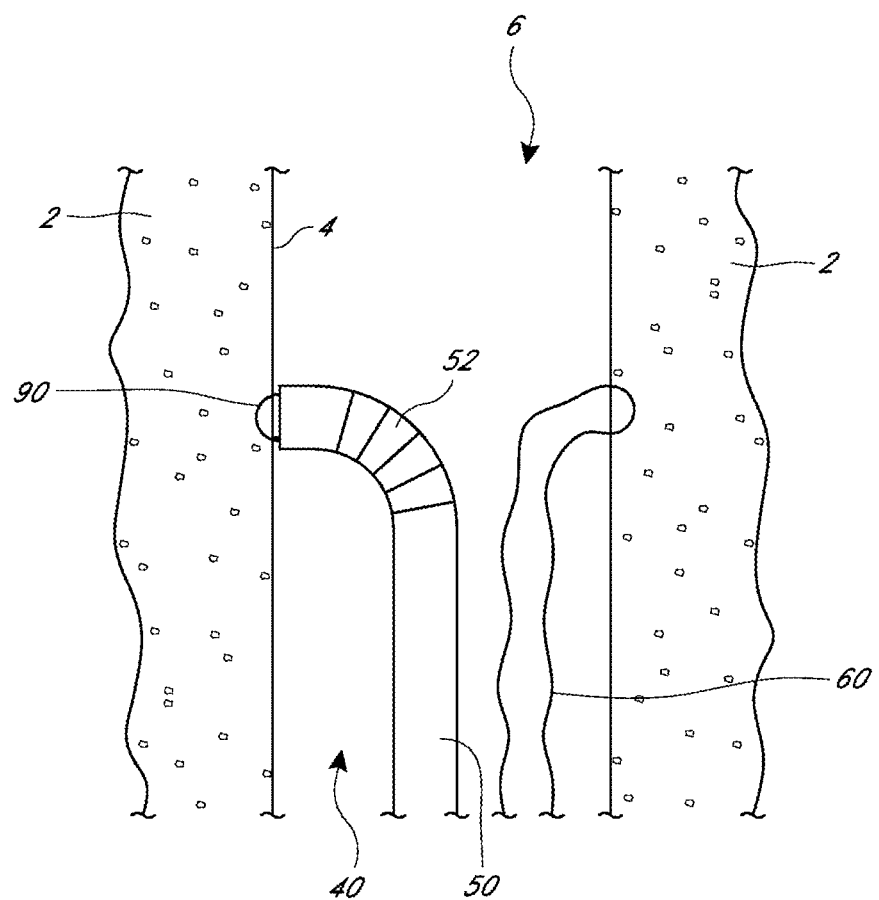
FIG. 13 is a schematic view as in FIG. 12 showing a needle in an extended position.

In FIG. 13, a needle 90 has moved from a retracted position to an extended position in which it passes through body tissue 2 and engages a suture portion (not illustrated). The needle 90 can then be withdrawn, bringing the suture portion with it through the body tissue and into the elongate body 50.

Figure 14:
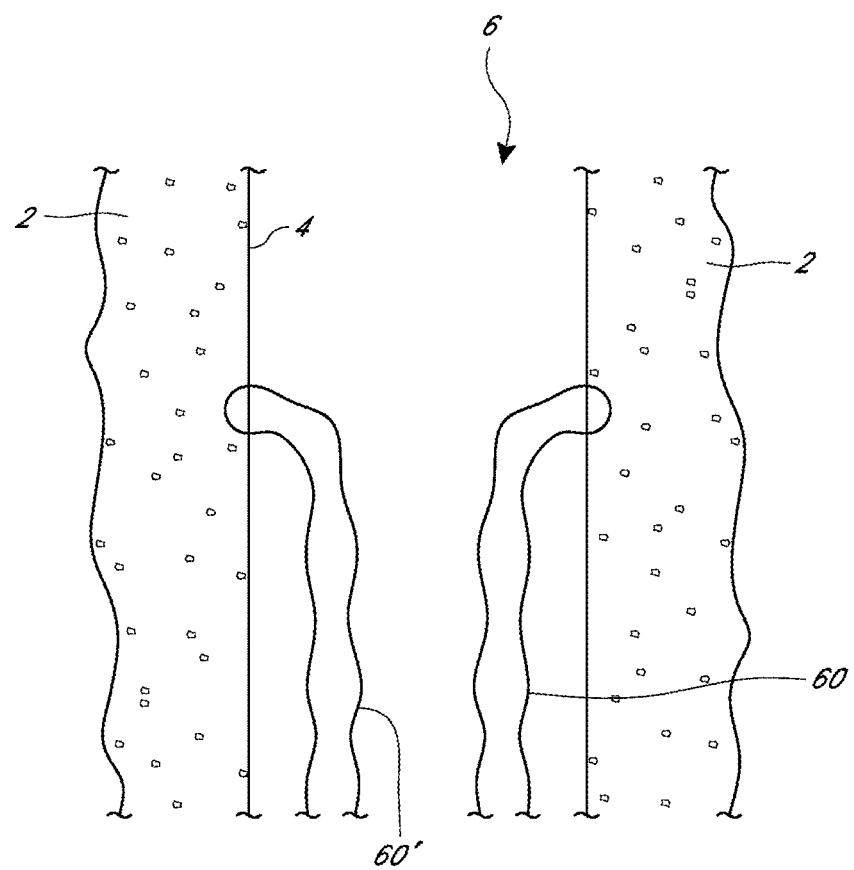
FIG. 14 is a schematic view as in FIG. 13 showing two lengths of suture running through body tissue.

In FIG. 14, the suturing device has been withdrawn from the lumen 6, leaving a first suture portion 60 and a second suture portion 60'. In some embodiments, the first suture portion 60 and second suture portion 60' can be lengths of the same suture. In some embodiments, they can be different suture portions and their ends can be connected together to form a single loop of suture. Further details regarding a device for joining sutures are provided in U.S. Patent Application Publication No. 2011/0190793, published on Aug. 4, 2011, which is hereby incorporated by reference herein in its entirety.

Figure 15:
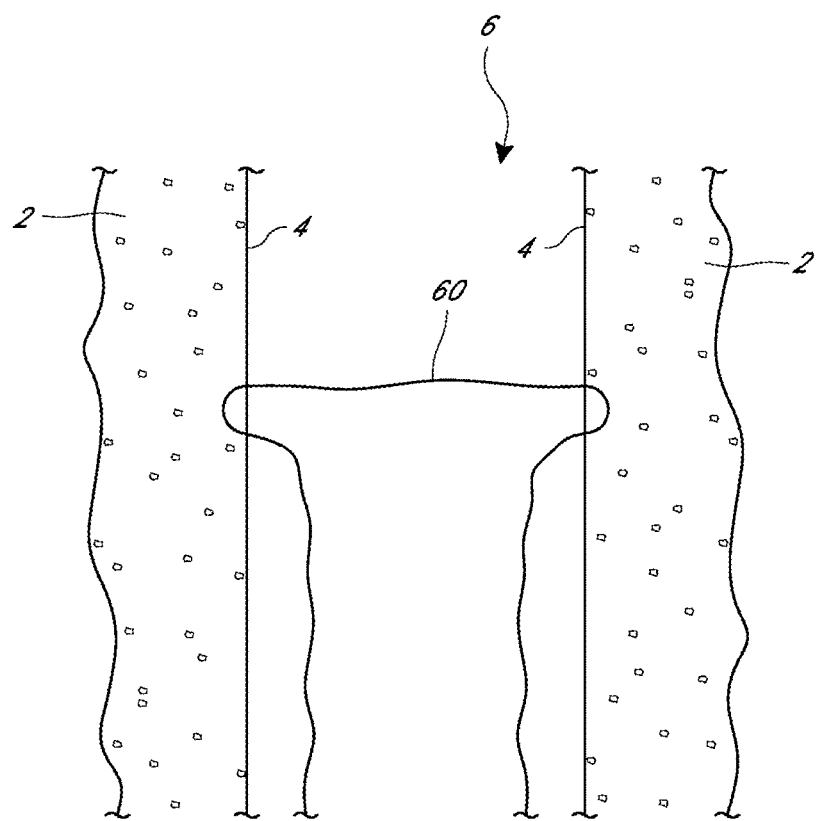
FIG. 15 is a schematic view as in FIG. 14 showing a length of suture extending across the body lumen.
Figure 16:
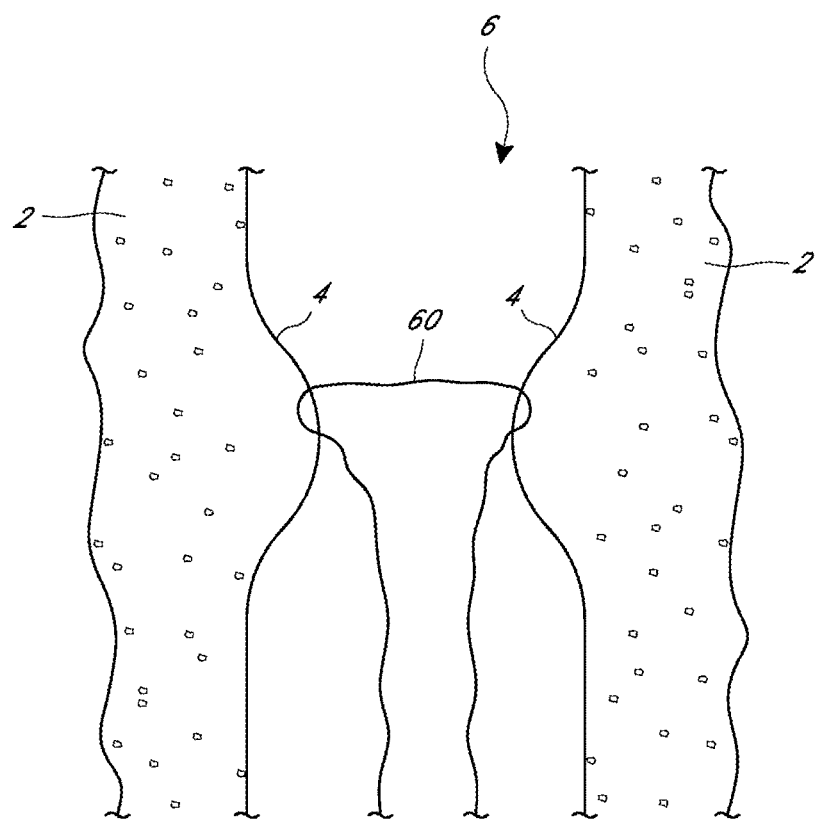
FIG. 16 is a schematic view as in FIG. 15 the length of suture closing the body lumen.

In FIG. 15, suture ends have been joined to form a single loop of suture 60 that passes through body tissue on opposite sides of the lumen 6, and the loose suture ends have been pulled to draw the loop into the body lumen. Pulling the loose suture ends further can draw opposing tissue walls 4 together, as illustrated in FIG. 16. This can constrict the body lumen 6. In some embodiments, the suture ends can be pulled even further to draw the opposite sides of the body lumen 6 into contact with each other to thereby close the lumen. In some embodiments, the illustrated suture portion 60 can represent one of a plurality of suture portions used to constrict and/or close off a body lumen. For example, in some embodiments, in addition to the illustrated suture portion 60, suture portions passing through opposing tissue walls 4 in planes different from the illustrated plane can be inserted according to methods described above and can be pulled to help close the body lumen in different planes.

From the foregoing description, it will be appreciated that inventive suturing devices and methods are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method of applying suture to an internal biological structure, the method comprising:
    delivering a distal facing surface at a distal tip of a suturing device to a position within a patient and against a section of tissue of the internal biological structure;
    advancing a needle from the distal facing surface into the section of tissue in a first direction;
    advancing the needle in a second direction different from the first direction and into engagement with a suture portion;
    retracting the needle back through the section of tissue to draw the suture portion through the section of tissue; and
    withdrawing the distal facing surface of the suturing device from the position against the section of tissue to be sutured;
    further comprising advancing a sheath distal to the suturing device to separate the distal facing surface of the suturing device from the section of tissue.

2. The method of applying suture to an internal biological structure of claim 1, wherein the needle is advanced into the section of tissue from a first side of the tissue and the needle passes out of the section of tissue through the first side of the tissue before engaging with the suture portion.

3. The method of applying suture to an internal biological structure of claim 1, wherein advancing the needle in the first direction and advancing the needle in the second direction is a continuous advancement.

4. The method of applying suture to an internal biological structure of claim 1, wherein advancing the needle comprises rotating the needle.

5. The method of applying suture to an internal biological structure of claim 1, wherein advancing the needle into the section of tissue comprises advancing the needle from a retracted position within the suturing device through the distal facing surface of the suturing device.

6. A method of suturing an internal body lumen, the method comprising:
    delivering a distal facing surface at a distal tip of a first suturing device into the body lumen;
    aligning the distal facing surface at the distal tip of the first suturing device with an inner wall of the body lumen against a first entry location;
    advancing a needle of the first suturing device from the distal facing surface through the inner wall in a first direction at the first entry location;
    advancing the needle of the first suturing device in a second direction different from the first direction and into engagement with a first suture portion;
    retracting the needle of the first suturing device back through the first entry location to draw the first suture portion through the inner wall;
    withdrawing the distal tip of the first suturing device from alignment with the inner wall at the first entry location;
    aligning a distal facing surface at a distal tip of a second suturing device with the inner wall of the body lumen against a second entry location on an opposite side of the body lumen as the first entry location;
    advancing a needle of the second suturing device from the distal facing surface of the second suturing device through the inner wall in a third direction at the second entry location;
    advancing the needle of the second suturing device in a fourth direction different from the third direction and into engagement with a second suture portion;
    retracting the needle of the second suturing device back through the second entry location to draw the second suture portion through the inner wall;
    withdrawing the distal tip of the second suturing device from alignment with the inner wall at the second entry location; and
    drawing the first suture portion through the inner wall closer to the second suture portion through the inner wall to thereby tighten the body lumen.

7. The method of suturing an internal body lumen of claim 6, wherein the first suturing device and the second suturing device are the same suturing device.

8. The method of suturing an internal body lumen of claim 6, wherein the first suture portion is joined with the second suture portion before the first suture portion through the inner wall is drawn closer to the second suture portion through the inner wall.

9. The method of suturing an internal body lumen of claim 6, further comprising withdrawing the first suturing device prior to aligning the distal facing surface at the distal tip of the second suturing device.

10. The method of suturing an internal body lumen of claim 6, wherein the first suture portion is within the body lumen when the needle of the first suturing device engages the first suture portion.

11. The method of suturing an internal body lumen of claim 6, further comprising advancing the needle of the first suturing device through the inner wall and into the body lumen at a first exit location different from the first entry location.

* * * * *

UNITED STATES PATENT AND TRADEMARK OFFICE
CERTIFICATE OF CORRECTION

Page 1 of 1

PATENT NO. : 11,779,324 B2
APPLICATION NO. : 16/688671
DATED : October 10, 2023
INVENTOR(S) : Anthony A. Nobles It is certified that error appears in the above-identified patent and that said Letters Patent is hereby corrected as shown below:

On the Title Page

On Page 6, Column 1, (item (56) U.S. Patent Documents), Line 57: Delete "4/2017" and insert -- 10/2017 --.

On Page 7, Column 1, (item (56) Other Publications), Line 22: Delete "byJohn" and insert -- by John --.

On Page 7, Column 2, (item (56) Other Publications), Line 12: Delete "B.SaundersCo.," and insert -- B. Saunders Co., --.

On Page 7, Column 2, (item (56) Other Publications), Line 22: Delete "Applicaton" and insert -- Application --.

On Page 7, Column 2, (item (56) Other Publications), Line 34: Delete "Isisolutions." and insert -- lsisolutions. --.

In the Specification

On Column 1, Line 6 (Approx.): Delete "continuation,"," and insert -- division --.

On Column 1, Line 11: Delete "APPARATUSES,"," and insert -- APPARATUSES," --.

Signed and Sealed this
Thirtieth Day of January, 2024

Katherine Kelly Vidal
*Director of the United States Patent and Trademark Office*